United States Patent [19]
Reitz

[11] Patent Number: 5,569,659
[45] Date of Patent: Oct. 29, 1996

[54] 4-ARYLPIPERAZINES AND 4-ARYLPIPERIDINES

[75] Inventor: Allen B. Reitz, Lansdale, Pa.

[73] Assignee: McNeilab, Inc., Spring House, Pa.

[21] Appl. No.: 442,600

[22] Filed: May 17, 1995

Related U.S. Application Data

[63] Continuation of Ser. No. 365,978, Dec. 28, 1994, abandoned, which is a continuation of Ser. No. 944,006, Sep. 11, 1992, abandoned, which is a continuation-in-part of Ser. No. 757,881, Sep. 11, 1991, abandoned.

[51] Int. Cl.$^6$ .............. A61K 31/495; A61K 31/55; C07D 401/00; C07D 403/00
[52] U.S. Cl. .............. 514/253; 514/252; 514/254; 514/212; 514/214; 544/295; 544/357; 544/230; 544/360; 544/363; 544/364; 544/366; 544/369; 544/370; 544/372; 544/379; 540/583; 540/598
[58] Field of Search ................ 544/295, 357, 544/360, 363, 364, 366, 369, 370, 372, 379, 230; 514/252, 253, 212, 214, 254; 540/583, 598

[56] References Cited

U.S. PATENT DOCUMENTS

| | | | |
|---|---|---|---|
| 3,988,371 | 10/1976 | Hansl | 544/357 |
| 4,362,738 | 12/1982 | Keck et al. | 544/418 |
| 4,510,140 | 4/1985 | Nardi et al. | 544/360 |
| 4,666,924 | 5/1987 | Stout et al. | 544/360 |
| 4,772,604 | 9/1988 | van Wijngaarden et al. | 544/372 |
| 4,782,061 | 11/1988 | Kruse et al. | 544/372 |
| 4,806,536 | 2/1989 | Cross et al. | 514/252 |
| 4,931,443 | 6/1990 | Nakao et al. | 544/374 |
| 4,992,441 | 2/1991 | Scott | 544/374 |

FOREIGN PATENT DOCUMENTS

A-066126 A1  12/1994  European Pat. Off.

*Primary Examiner*—Cecilia Tsang
*Attorney, Agent, or Firm*—Ralph R. Palo

[57] ABSTRACT

Compounds of the general formula I:

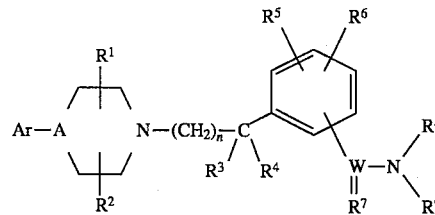

are disclosed as novel antipsychotic agents.

30 Claims, No Drawings

4-ARYLPIPERAZINES AND 4-ARYLPIPERIDINES

This is a continuation of application Ser. No. 08/365,978, filed Dec. 28, 1994, now abandoned, which is a continuation of application Ser. No. 07/944,006 filed Sep. 11, 1992, now abandoned which is a continuation-in-part of application Ser. No. 757,881 filed Sep. 11, 1991, now abandoned.

BACKGROUND OF THE INVENTION

Antipsychotic drugs are known to alleviate the symptoms of mental illnesses such as schizophrenia. Examples of such drugs include phenothiazine derivatives such as promazine, chlorpromazine, fluphenazine, thioridazine and promethazine, thioxanthenes such as chlorprothixene, butyrophenones such as haloperidol and clozapine. While these agents may be effective in treating schizophrenia, virtually all except clozapine produce extrapyramidal side effects, such as facial tics or tardive dyskinesia. Since antipsychotics may be administered for years or decades to a patient, such pronounced side effects may complicate recovery and further isolate the individual from society.

Compounds having some structural similarity to those of the present invention are described in EPO application 88,309,581.2, U.S. Pat. Nos. 4,772,604; 4,782,061; 4,362,738; 3,988,371; 4,666,924; 4,931,443; and 4,992,441. Other somewhat similar compounds are disclosed in *J. Clin. Chem. Clin. Biochem.* 1988, 26, 105 and *J. Med. Chem.*, 1991, 34, 2133.

The present invention describes novel compounds that combine antipsychotic effects with minimal or reduced side effects such as extrapyramidal symptomology, and increased acid stability relative to some of the compounds known in the art.

SUMMARY OF THE INVENTION

Compounds of the general formula I:

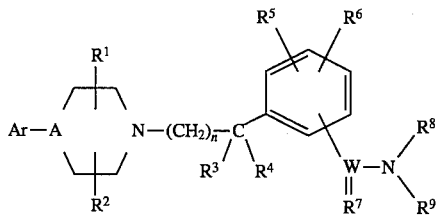

wherein Ar, W, A, $R^1$, $R^2$, $R^3$, $R^4$, $R^5$, $R^6$, $R^7$, $R^8$, $R^9$ and n, as defined hereinafter, are potent antipsychotic agents useful in the treatment of psychotic conditions such as schizophrenia in animals and humans. Many of these exhibit a reduced tendency to induce extrapyramidal side effects and/or improved acid stability when compared with prior art compounds. The compounds of the present invention may also be useful in the treatment of other disorders of the central nervous system such as anxiety and aggression. In addition, certain of the compounds represented by formula I are useful in the treatment of constipation, diarrhea, emesis, and hypertension. The compounds of the present invention may also have other wide reaching therapeutic uses.

DETAILED DESCRIPTION OF THE INVENTION

The present invention is directed to compounds represented by the general formula I:

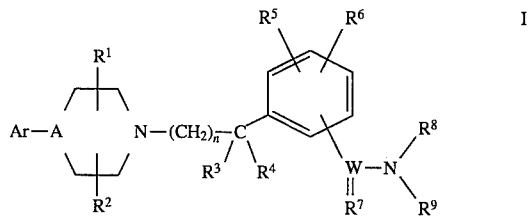

wherein

A is N or CH.

W is C or SO.

$R^1$ and $R^2$ are independently selected from any of H or $C_1$–$C_4$ alkyl, n=0–4.

$R^3$ and $R^4$ are either both H, or one of them is H and the other is $C_1$–$C_4$ alkyl or hydroxyl, or both are taken together as oxygen to constitute a carbonyl group; with the proviso that when n=0 both $R^3$ and $R^4$ cannot be taken together to constitute a carbonyl.

$R^5$ and $R^6$ are independently selected from any one of H, $C_1$–$C_8$ alkyl, $C_1$–$C_8$ alkoxy, nitro, halogen, haloalkyl, $C_1$–$C_8$ alkylthio, amino, $C_1$–$C_8$ mono- or di-alkyl amino, or $C_1$–$C_8$ alkylamido. Preferably, $R^5$ and $R^6$ are independently selected from any one of H, $C_1$–$C_8$ alkyl, $C_1$–$C_8$ alkoxy, nitro, amino, or $C_1$–$C_8$ alkylamido.

$R^7$ is O or S where W is C; $R^7$ is O where W is SO.

$R^8$ and $R^9$ are independently selected from any one of H, $C_1$–$C_8$ alkyl, phenyl, substituted phenyl, aralkyl wherein the alkyl portion is $C_1$–$C_8$, alkoxycarbonylamido, acyl, $C_3$ to $C_{10}$ cycloalkyl; or —$NR^8R^9$ may be taken together to form a ring having 4–10 ring atoms, preferably 4–8 ring atoms, which ring may be saturated or unsaturated, preferably saturated, substituted or unsubstituted, and may contain up to one more hetero atom in addition to the ring N, such as S, O or N within the ring, more preferably, the additional hetero atoms are N or O, even more preferably, the additional hetero atom is O and most preferably, there are no additional hetero atoms; or optionally the —$NR^8R^9$ ring may be combined with a 2–4 membered carbon moiety to form a fused bicyclic ring, which may be saturated or unsaturated, and unsubstituted or substituted; or optionally the $NR^8R^9$ ring may be combined with a four membered moiety containing at least two carbon atoms and up to two hetero atoms selected from S or O, but preferably selected from O, to form a spirocycle ring system which may be saturated or unsaturated, preferably saturated, substituted or unsubstituted. More preferably, the 2–4 membered carbon moiety is combined with a —$NR^8R^9$ ring which contains 5–7 ring atoms with the N being the only hetero atom in the ring, thereby forming a fused ring system. Most preferably, the —$NR^8R^9$ ring is saturated prior to being fused with the 2–4 membered carbon moiety.

Ar is aryl such as phenyl or napthyl, heteroaryl or substituted aryl wherein aryl may be independently substituted with one or more of $C$–$C_8$ alkyl, cycloalkyl, hydroxyalkyl, $C_1$–$C_8$ alkoxy, aryloxy, hydroxyl, trifluoromethyl, trifluoromethoxy, cyano, $C_1$–$C_8$ alkylthio, halogen, nitro, $C_1$–$C_8$ haloalkyl, amino or $C_1$–$C_8$ mono- or di-alkylamino. Alkoxy, such as i-propoxy or methoxy is presently the preferred substituent. As a halogen, the substitution is preferably fluorine, chlorine, or bromine. Optionally present hydroxyl or hydroxyalkyl groups may be esterified or etherified. Examples of suitable heteroaryl rings are pyrimidinyl, pyridinyl, pyridazinyl, pyrazinyl, imidazyl, pyrrole, furan, thiophene, triazolyl, and thiazolyl. The preferred heteroaryl rings are pyrimidinyl and pyridinyl. More preferably, Ar is substituted phenyl.

Ar may also be a fused ring system of the formula II:

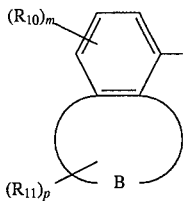

wherein B together with the 2 carbon atoms of the phenyl group forms an entirely or partly unsaturated cyclic group having 5–7 ring atoms and within the ring 0–3 hetero atoms from the group O, S and N may be present with the proviso that the sum of the number of oxygen atoms and sulfur atoms is at most 2, and that the nitrogen atoms in the ring may be substituted with $R^{12}$ selected from any one of H, $C_1$–$C_8$ alkyl, hydroxyalkyl or $C_1$–$C_8$ acyl;

$R^{10}$ and $R^{11}$ may be independently selected from any one of alkyl, cycloalkyl, phenyl, substituted phenyl or heteroaryl, hydroxyalkyl, alkoxyalkyl, alkoxy, aryloxy, alkylthio, arylthio, mono- or di-alkylamino, mono- or di-arylamino, hydroxyl, amino, alkyl-, alkoxy-, amino-, or mono- or di-alkylamino-carbonyl, nitro, cyano, halogen, trifluoromethyl, trifluoromethoxy, amino or mono- or di-alkylaminosulfonyl. $R^{10}$ may also be an oxo or thioxo group. Variable m has the value 0–3 and p has the value 0–2. More preferably, $R^{10}$ and $R^{11}$ are selected from any of alkoxy, halogen or cyano.

More preferred values for the moiety of formula II are: B forms together with the two carbon atoms of the phenyl group an entirely or partly unsaturated ring consisting of 5 atoms, which ring comprises at least one oxygen atom. $R^{10}$ and $R^{11}$ are alkyl, alkoxy, hydroxyl, nitro, cyano, halogen, or trifluoromethyl. $R^{10}$ and $R^{11}$ are more preferably selected from any of alkoxy, halogen or cyano. $R^{10}$ is preferably in the meta or ortho position in relation to the piperazine/piperidine group. Variables m and p have the value 0–2. A particular preferred subgensis of such compounds are those wherein m and p each have a value of 0.

When $R^{10}$ or $R^{11}$ comprises an alkyl group, it is preferably a straight or branched alkyl group having 1–5 carbon atoms. As a cycloalkyl group, the groups $R^{10}$ or $R^{11}$ comprise a ring system having 3–7 ring atoms and not more than 10 carbon atoms including any substituents as a whole. When $R^{10}$ or $R^{11}$ is a hydroxyalkyl group such a group preferably comprises 1–5 carbon atoms. As a halogen atom, $R^{10}$ or $R^{11}$ preferably is fluorine, chlorine or bromine. Optionally present hydroxyl or hydroxyalkyl groups may be esterified or etherified.

When $R^{10}$ or $R^{11}$ is substituted phenyl it may be substituted with one or more of $C_1$–$C_8$ alkyl, $C_1$–$C_8$ alkoxy, halogen, trifluoromethyl, $C_1$–$C_8$ alkylthio, di-alkylamino (wherein each alkyl is $C_1$–$C_8$), $C_1$–$C_8$ alkylamino, nitro or mono- or di-alkylamino sulfonyl (wherein each alkyl is $C_1$–$C_8$).

When —$NR^8R^9$ are taken together to form a ring, a fused ring system or a spirocycle ring system, such rings may be substituted with one or more of $C_1$–$C_8$ alkyl, $C_1$–$C_8$ alkoxy, phenyl, substituted phenyl (wherein phenyl may be substituted with any of the substituents listed for $R^{10}$ or $R^{11}$ substituted phenyl), hydroxy, aralkyl such as benzyl, wherein the alkyl portion is $C_1$–$C_8$, oxo or thioxo. The preferred substituents for the —$NR^8R^9$ ring are $C_1$–$C_8$ alkyl, hydroxy or oxo. The preferred substituents for the fused ring system are $C_1$–$C_4$ alkoxy. The spirocycle ring system is preferably unsubstituted and saturated.

Examples of preferred ring systems wherein —$NR^8R^9$ are taken together to form a ring having 4–10 ring atoms include pyrrolidine, piperidine, hexahydroazepine, octahydroazocine, oxazine and 2,6-dimethylpiperidine.

Examples of preferred fused ring systems for —$NR^8R^9$ are represented by formulas III and IV:

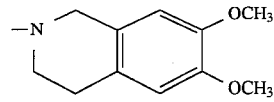

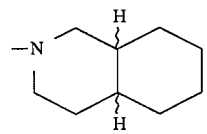

As used herein for the definition of —$NR^8R^9$, a spiro ring system is a 2 ring system, the union of which is formed by a single atom which is the only common member of the two rings. A particularly preferred spirocycle ring is represented by the formula V:

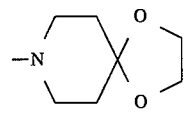

As used herein, unless otherwise noted alkyl and alkoxy whether used alone or part of a substituent group, include straight and branched chains. For example, alkyl radicals include methyl, ethyl, propyl, isopropyl, n-butyl, isobutyl, sec-butyl, t-butyl, n-pentyl, 2-methyl-3-butyl, 1-methylbutyl, 2-methylbutyl, neopentyl, n-hexyl, 1-methylpentyl, 2-methylpentyl. Alkoxy radicals are oxygen ethers formed from the previously described straight or branched chain alkyl groups. Of course, if the alkyl or alkoxy substituent is branched there must be at least 3 carbon atoms.

The term "aryl" as used herein alone or in combination with other terms indicates aromatic hydrocarbon groups such as phenyl or naphthyl. The term "heteroaryl" means aromatic hydrocarbon groups containing 1 or 2 hetero atoms selected from any of S, O or N. The term "aralkyl" means a $C_1$–$C_8$ alkyl group substituted with an aryl group. The term acyl unless otherwise specified herein means a benzoyl or a $C_1$–$C_8$ alkanoyl group, which can be optionally substituted. With reference to substituents, the term independently means that when more than one of such substituent is possible such substituents may be the same or different from each other.

Compounds according to this invention have a 1,2-, 1,3- or 1,4-relationship of the W substituent with the —$C(R^3)(R^4)$— group on the W-bearing phenyl ring. Preferred compounds have a 1,2- or 1,3-relationship of these two groups. The $R^5$ and $R^6$ substituents may be located in any of the other unsubstituted ring positions.

A particularly preferred subgenus of compounds of the formula I are those of the formula (Ia):

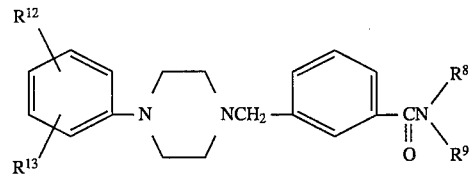

wherein $R^8$ and $R^9$ are as defined above and $R^{12}$ and $R^{13}$ are as defined as substituents for Ar in formula I. Preferably $R^8$ and $R^9$ are taken together with the N to form a saturated ring having 5–8 ring atoms and one of $R^{12}$ and $R^{13}$ is $C_1$–$C_8$ alkoxy and the other is H. The most preferred $C_1$–$C_8$ alkoxy group is i-propoxy or methoxy.

Examples of particularly preferred compounds include:

1-[3-[[4-[2-(1-Methylethoxy)phenyl]-1-piperazinyl]methyl]benzoyl]piperidine succinate;

Hexahydro-1-[3-[[4-[2-(1-methylethoxy)phenyl]-1-piperazinyl]methyl]benzoyl]-1H-azepine monohydrochloride;

1-[3-[[4-(1,4-Benzodioxan-5-yl)-1-piperazinyl]methyl]benzoyl]piperidine perchlorate (5:7);

1-[2-[[4-[2-(1-Methylethoxy)phenyl]-1-piperazinyl]methyl]benzoyl]piperidine dhydrochloride;

1-[3-[[4-[2-(1-Methylethoxy)phenyl]-1-piperazinyl]methyl]-benzoyl]-2,6-dimethylpiperidine hydrochloride (3:2); and 1-[3-[[4-[2-(1-Methylethoxy)phenyl]-1-piperidinyl]methyl]benzoyl]piperidine monohydrochloride.

The invention definition of formula I includes racemates and individual isomers, e.g. as caused by the presence of a stereogenic carbon such as when a substituent would be 2-butyl. Also within the scope of the invention are compounds of the invention in the form of hydrates and other solvate forms.

Representative salts of the compounds of formula I which may be used include those made with acids such as hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzene-sulfonic, p-toluenesulfonic, cyclohexanesulfamic, salicyclic, p-aminosalicyclic, 2-phenoxybenzoic, 2-acetoxybenzoic or a salt made with saccharin. Such salts can be made by reacting the free base of formula I with the acid and recovering the salt.

The compounds of formula I may be prepared according to Reaction Scheme 1:

Reaction Scheme 1

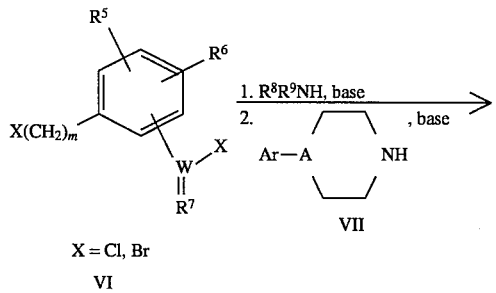

As shown, the 1,2-, 1,3-, and 1,4-disubstituted benzamides or sulfonamides may be prepared by a sequential reaction with the appropriate haloalkyl benzoyl halide or haloalkyl benzenesulfonyl halide. The first condensation with the requisite amine is conducted in a non-protic solvent such as tetrahydrofuran (THF) with cooling (e.g. in the range −78° C. to 5° C.), being careful not to let the solution exotherm so as to avoid reaction of the haloalkyl functionality. The base present in the reaction (for the removal of the HX formed) is typically a tertiary amine such as triethyl amine or diisopropyl ethyl amine, or it could be a molar excess (at least) of the amine reactant (e.g. $R^8R^9NH$). The intermediate haloalkyl benzamide thus formed could be then taken on directly to the product by reaction with the aryl piperazine or aryl piperidine, or it could be isolated after an extractive workup and/or chromatography. If the intermediate was carried on in situ to the product in THF, heating (30° C.–67° C.) is generally required for complete reaction. If the intermediate is isolated and then reacted separately with the aryl piperazine or aryl piperidine, the optimal solvents are dipolar aprotic solvents such as dimethylformamide (DMF) or N-methyl-2-pyrrolidinone. The base used in this latter step could be a tertiary amine or potassium or sodium carbonate. Using the two-step method (i.e. isolation of the intermediate), the product could in some cases be obtained pure after recrystallization as a salt without resort to chromatography.

1,2- and 1,3-halomethylbenzoyl halides used when m=1 in Reaction Sheme 1 are commercially-available from Fluka, Carbolabs or Pfaltz and Bauer, or could be prepared by literature methods or modifications thereof. (See e.g.: Ger. Offen. 2,835,440, 28 February 1980; and J. Johnson and I. Pattison *J. Hetero. Chem.* 1986, 23, 249). Halomethyl benzoyl halides bearing substituents have also been described in the literature, such as in the methoxy-substituted case cited in R. Quelet et al. *Bull. Soc. Chem., France* 1969, 1698. The final products are typically chromatographed to achieve purity, and then converted to an acceptable salt form.

The 1,3- or 1,4-disubstituted analogs may be prepared in the same manner as the derivatives shown above. There are alternative methods for the preparation of compounds of this type. For example, they may be synthesized by a palladium-mediated coupling of a bromoaryl derivative with carbon monoxide and piperidine (*J. Org. Chem.* 1974, 39, 3327) as shown in Reaction Scheme 2 for a 1,4-disubstituted case.

Reaction Scheme 2

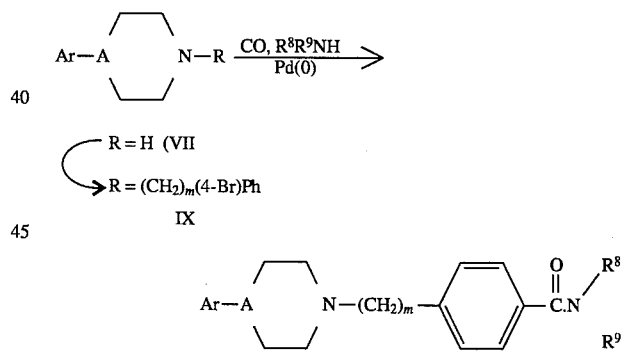

The preparation of the sulfonamide analogues (W=SO, $R^7$=O, and n=0 in I) require preparation of the necessary halomethyl sulfonyl halide by halogenation of the appropriate toluenesulfonyl halides on the benzylic methyl position with N-bromosuccinimide mediated by benzoyl peroxide. The halomethyl sulfonyl halides were used in generally the same manner as for the benzoyl halide case (e.g. see Reaction Scheme 1).

Many aryl piperazines are commercially available from Aldrich Chemical Company or may be prepared by standard methods known in the art (for example see G. E. Martin et al. *J. Med. Chem.* 1989, 32, 1052). These piperazines (VII, A=N) may be obtained according to the following Reaction Scheme 3 where Ar is as described in connection with formula I and Z is a leaving group such as halo (e.g. chloro):

Reaction Scheme 3

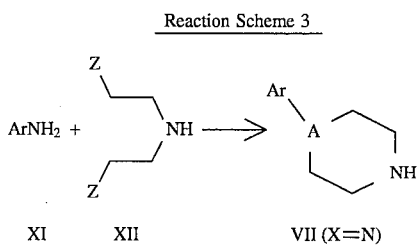

In carrying out Reaction Scheme 3, an amine XII is heated with an aniline or an aromatic heterocyclic primary amine XI at about 50° to 150° C. in a solvent such as n-butanol with recovery of the piperazine VII (A=N).

Piperazines of formula VII (A=N) where Ar is a formula II moiety are described as formula (2) in U.S. Pat. No. 4,782,061 published earlier as EPO 185,429 and EPO 190, 472 on Jun. 15, 1986 and Aug. 13, 1986, respectively, which documents are hereby incorporated by reference. Other piperazines of formula VII (A=N) where Ar is a formula II moiety are described as formula 29 in EPO 138,280 published Apr. 24, 1985 which is incorporated by reference.

The piperazine employed for the preparation of compounds #30 and 31 in Table 2 was prepared by the method of I. van Wijngaarden et al. (*J. Med. Chem.* 1988, 31, 1934). The piperidine used in the preparation of compounds #15 and 38–41 was prepared by the method shown in Reaction Scheme 4.

Reaction Scheme 5

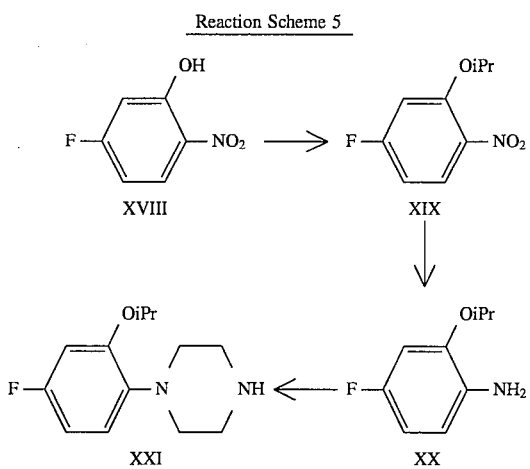

The piperazines required to prepare 2-fluoropiperazinyl compounds #9 and 10 were prepared by nucleophilic displacement of 1,2-difluorobenzene with the requisite piperazine such as in reaction of 2,5-dimethylpiperazine with 1,2-difluorobenzene in the presence of sodium amide. Alternatively, certain compounds of the invention can be prepared by the method shown in Reaction Scheme 6.

Reaction Scheme 4

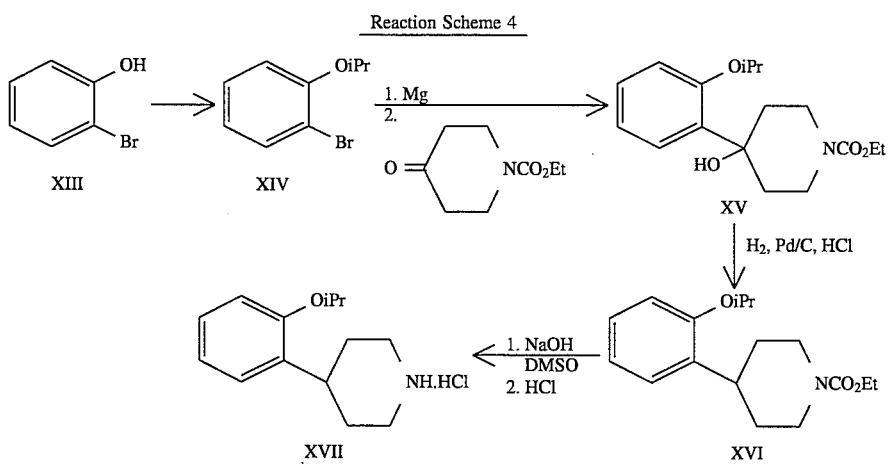

The piperazine utilized for the synthesis of compounds #78–80 was synthesized as shown in Reaction Scheme 5.

Reaction Scheme 6

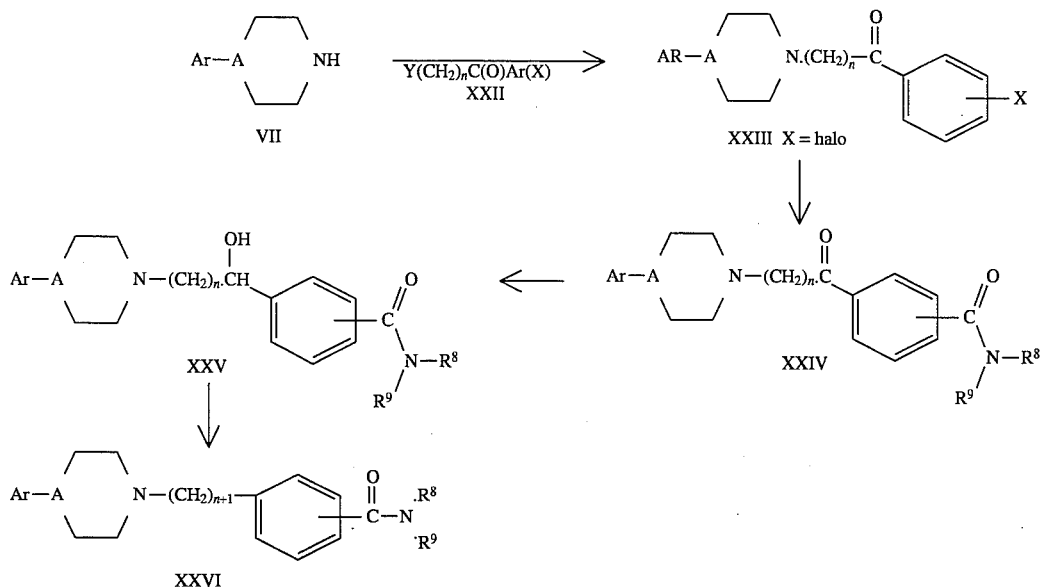

Aryl piperazines VII (A=N) can be condensed with compounds XXII in which Y represents a leaving group suitable for a diplacement reaction (e.g. halogen, p-toluenesulfonate, trifluoromethanesulfonate) to give compounds XXIII. This deplacement reaction is typically carried out in a dipolar aprotic solvent such as DMSO or DMF, using sodium carbonate, potassium carbonate, or a tertiary amine [e.g. triethylamine or di(isopropyl)ethylamine] as the base, generally with heating (30°–80° C. for 2 h to 4 d). The resulting ketone (XXIII) can be converted to amide XXIV by the aminocarbonylation reaction described for Reaction Scheme 2. Reduction of the carbonyl group of XXIV by the use of sodium borohydride in alcoholic solvents (EtOH, iPrOH) at room temperature (2–30 h) can gave alcohol XXV. Further reduction of XXV by the method of catalytic hydrogenation ($H_2$, palladium/carbon) in alcoholic solvents (e.g. EtOH), in the presence added mineral acid (e.g. HCl) to facilitate the reaction, can afford compounds XXVI.

Compounds of the invention can also be prepared by the chemistry shown in Reaction Scheme 7.

Carbonyl compound XXVII is reacted with compounds VII in a reductive amination reaction to give compounds XXVIII. This reaction can be carried out using sodium borohydride in titanium isopropoxide. It can also be conducted by forming an imine from VII and XXVII and then reducing it catalytically with hydrogen in the presence of a noble metal catalyst (e.g. palladium or platinum). Hydrolysis of the nitrile functionality of XXVIII to give XXIX is carried out in the presence of sodium hydroxide or potassium hydroxide, usually at reflux in an alcoholic solvent. Compound XXIX is then combined with $R^8R^9NH$ to form amide XXX, using one of the standard reactions to accomplish this transformation such as the use of dicyclohexylcarbodiimide or carbonyl diimidazole.

The antipsychotic activity of the compounds of the invention may be determined by the Block of Conditioned Avoidance Responding (Rat) test (CAR), references being Cook, L. and E. Weidley in *Ann. N.Y. Acad. Sci.*, 1957, 6, 740–752, and Davidson, A. B. and E. Weidley in *Life Sci.*, 1976, 18, 1279–1284. This test was performed for compounds dis-

REACTION SCHEME 7

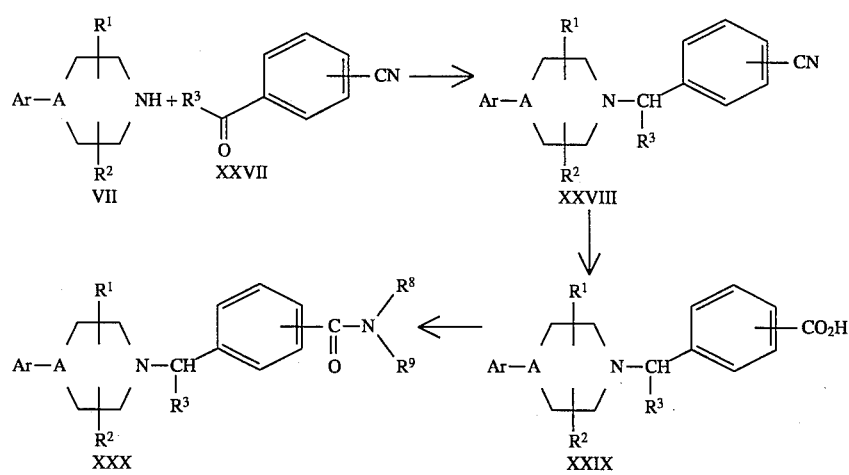

closed in this invention, and the data are listed in Tables 1–5. A reading of –20% in the CAR test was generally taken to represent a minimum value for a compound to be designated as active at a given dose. In addition the affinity of the compounds for several receptors found in the central nervous system was evaluated; the affinity for the D-2 (dopamine-2) receptors is also listed in Tables 1–5. As modulation of this receptor is generally recognized to be beneficial in the treatment of schizophrenia (G. P. Reynolds *Trends Pharmacol Sci.* 1992, 13, 116), affinity for this receptor indicates potential utility for the compounds. A D-2 affinity of 1000 nM or less has been taken as predictive of antipsychotic activity. As a class, the compounds of the present invention also display a remarkably low cataleptogenic response in rats. The catalepsy test is taken to evaluate the liability of anti-psychotics to produce extra-pyramidal side effects. Representative data for several of the preferred compounds at a single dose are given in Table 6. The only compounds which to date have not exhibited potential antipsychotic activity in either of the screens in which they have been tested are compounds #8, 20, 24, 27, 36, 37, 47, 48, 65 and 87. Of these, only compounds #8, 20, 24, 47 and 48 have not exhibited activity in any of the other non-antipsychotic screens in which they have been tested to date.

Compounds #53 and 54 have been found to be particularly potent inhibitors of apomorphine-induced emesis in the dog, and those data are shown in Table 7. This latter test is used in the preclinical evaluation of antipsychotics, and it also implies that the compounds could be used clinically for the treatment of emesis.

Certain of the compounds of the present invention also have been demonstrated to be useful in the treatment of constipation and in the treatment of diarrhea and/or irritable bowel syndrome as shown in Table 8. The test used to determine this activity is a Rat Glass Bead Test, described below.

Compounds #37 and 87 were also evaluated in the fully recovered, unanesthetized, unrestrained spontaneously hypertensive rats (SHR model) which is described hereinafter. They were deemed to be active because at doses of 30 mg/kg p.o. they caused a drop in the mean arterial pressure. For compound #37 the drop was 26 mm of mercury with an onset of 0.5 h and a duration of 3.5 h. For compound no. 87 the drop was 37 mm of mercury with an onset of 0.25 h and a duration of 5.75 h.

Block of Conditioned Avoidance Responding (Rat)

Apparatus: Rat operant chambers, housed within sound attenuated booths, both from Capden Instruments Ltd., were used in this test. The test chamber (8" H×9⅜" W×9" D) is constructed of aluminum and plexiglass with floor grid bars of stainless-steel (⅛" O.D.) spaced 9/16" apart. A stainless-steel operation level 1½" wide projects ¾" into the chamber and is positioned 2⅝" above the grid floor. The shock stimulus is delivered via the grid floor by a Coulbourn Instruments solid state module. The parameters of the test and the collection of data are controlled automatically.

Training: Male, Fischer 344 rats obtained from Charles River (Kingston, N.Y.) weighing more than 200 g, are individually housed with chow and water provided ad libitum. The rats are trained for two weeks to approach criterion levels in the avoidance test (90% avoidance rate). One-hour training sessions are run at about the same time each day for four or five days a week. The training session consists of 120 trials, with the conditioned stimuli presented every 30 sec. A trial begins with presentation of the conditioned stimuli (a light and a tone). If the rat responds by depressing the operant lever during the 15-second presentation of the conditioned stimuli, the trial is terminated and the animal is credited with a CAR. Failure to respond during the conditioned stimuli causes the presentation of the unconditioned stimulus (UCS), a 0.7 mA shock which is accompanied by a light and tone for five seconds. If the rat depressed the lever within the ten-second period, the shock and tdal are terminated and an escape response recorded. If the rat fails to depress the lever during the UCS (shock), the trial is terminated after ten seconds of shock and the absence of a response is scored as a failure to escape. Intertrial level presses have no effect. If a rat performs at the 90% CAR level for two weeks, it is then run twice a week on the test schedule (see below) until baseline performance stabilized. Before any drug is administered, two weeks of CAR at a rate of 90% or better is required.

Determination of $ED_{50}$ Values

Trained rats are run in a one-hour session on two consecutive days at the same time and in the same test chamber each day. The sessions consist of 60 trials, one every minute. The conditioned stimuli are presented for 15 sec (maximum) and the unconditioned stimuli five sec (maximum). On Day 1, a vehicle solution is administered to the rats at a time preceding the trial run corresponding to the pretreatment time for the test compound. The route of administration and the volume of vehicle are also matched to that of the test compound. Only animals that exhibited greater than 90% CAR on Day 1 are given the test compound on Day 2.

Statistical Computations: $ED_{50}$ values (that dose required to reduce the mean number of CARS to 50% of the control mean) are determined in the following manner. The percent change in CAR on the drug treatment day compared to vehicle pretreatment day is the key measure. The percent change (% change) in CAR is determined using the following formula:

% change CAR=((% CAR for Day 2/% CAR for Day 1)×100)–100

A negative number indicates a blockade of CAR, whereas a positive number would indicate increased CAR. The test results are reported as the mean % change for the group of rats. Failure to escape, a measure of the general sedative potential of the compound, was calculated for each animal as follows:

% Failures=# of Failures to Escape/# of trials

The % failures, viz., loss of escape, is also reported as a group mean. Failures to escape are monitored closely and a session is terminated if ten failures occurred. $ED_{50}$ values and 95% confidence limits are calculated using linear regression analysis. The results of the CAR tests are shown in Tables I–5.

In the Tables and formulas therein, OiPr is isopropoxy, Me is methyl, MeO is methoxy, Et is ethyl, Ph is phenyl, n-Bu is normal butyl, $cC_6H_{11}$ is cyclohexyl, BOC is t-butyloxycarbonyl, Ac is acetyl, and NT is not tested in that particular test. The escape loss numbers are shown at CAR 5 mg/kg unless otherwise noted. Where the Salt Form column is filled in with a hyphen, this indicates that the compound was evaluated as the free base. Where the M.p. column is filled in with a hyphen, this indicates that the compound was an oil at room temperature.

Receptor Binding Assay

The dopamine $D_2$ binding activity of compounds was determined using a $P_2$ fraction (synaptosomal membranes) prepared from male, Wistar rats. The $D_2$ assay employed a $P_2$ fraction from the striatum, the ligand $^3H$-spiperone at a concentration of 0.05 nM, and 1 mM haloperidol as a blank determinant. Incubation was in 3 mM potassium phosphate buffer for 45 min at 37° C. Under these conditions, specific binding constituted 75% of total binding, and the $K_I$ values for some known drugs were: 0.37 nM for haloperidol and 82 nM for clozapine.

The data from this assay were analyzed by calculating the percent inhibition of the binding of the tritiated ligands by given concentrations of the test compound. $K_I$ values, where given, were obtained from the logit analysis of concentration-inhibition curves.

Catalepsy Test in Rats

The catalepsy test was performed as described in Clineschmidt, B. V.; McKenry, M. A.; Papp, N. L.; Pflueger, A. B.; Stone, C. A.; Totaro, J. A.; Williams, M. J. *Pharm. Exp. Therap.* 1979, 208, 406–476. The forepaws of male, Sprague-Dawley rats obtained from Charles River (170–240 g) were gently placed on a black cork (3.5 cm high) and the time until the forepaw was removed was recorded. Each rat was given three trials with a maximum time of 60 sec on the cork. The sum of the three trials was taken as the score for each rat. Percent catalepsy was defined as the percent of 180 sec (maximum time) that a rat permitted its forepaw to rest on the cork. Pretreatment times of 60 min and 240 min were used on a routine basis. In each test session, two control groups were used; animals treated with saline (or vehicle) served as a negative control and animals treated with haloperidol were a positive control. The dose-response relationship for a compound was determined at the time of maximum catalepsy (60 or 240 min). The results of this test are shown in Table 6.

Block of Apomorphine-Induced Emesis In Dogs

This procedure was modified from that described in Janssen, P. A. J.; Niemegeers, C. J. E.; Schellekens, K. *Arzn.-Forch.* 1965, 15, 1196–1206. The animals were treated with a test dose of apomorphine HCl to produce retching, and the effectiveness of a test compound in blocking that retching is determined. This effectiveness is normally a consequence of dopamine antagonism (Niemegeers, C. J.; Janssen, P. A. *J. Life Sciences.* 1976, 24, 2201–2216). Animals were deprived of food for at least 16 h before testing, but they were allowed free access to water. Following one of several pretreatments, a challenge dose of 1 mg/kg apomorphine HCl s.c. was given and the number of retches that occurred during the following 20 min period was recorded. At the start of the series, and after one week on testing, all dogs were pretreated with saline before the challenge dose of apomorphine HCl was administered. All of the saline-pretreated animals retched. During the course of the study; each dog was tested between 5 and 11 times with 2–21 days between testing. Data were analyzed to determine the $ED_{50}$ dose for blocking apomorphine HCl-induced emesis. The dose calculated to block retching in 50% of the animals and the 95% confidence limits were determined with PROBIT analysis. The results of this test are shown in Table 7.

Rat Glass Bead Test

The rat glass bead test is used to evaluate the action of compounds on propulsive motility of the distal colon. Male Charles-River rats weighing 50–90 grams are fasted for at least 18 hours in individual cages with water provided. Groups of rats are then dosed by the indicated route at the appropriate pretreatment time. A 4 mm glass bead is then inserted 3.5 cm into the distal colon through the anus using a 4 mm diameter glass rod. Rats are then placed in open top glass jars and observed for 60 minutes. The time for expulsion of the bead is noted for each rat. Rats not expelling the bead after 60 minutes are necropsied and the presence of the bead in the colon confirmed. Expiration times of 0–15 min signify potential use in the treatment of constipation. Values of 40–60 min suggest utility in the treatment of diarrhea. Values of 16–39 are taken to show inactivity in this test. Data are presented as mean expulsion times and standard error of the means in Table 8. Statistical analysis is done using one way analysis of variance and Fisher's LSD comparison. A probability of less than 0.05 is considered to be statistically significant.

Spontaneously Hypertensive Rat Test (SHR)

Adult male 350–450 g SHR [Tac:N(SHR)FBR], Taconic Farms, Germantown, N.Y. are prepared for direct measurement of arterial pressure, housed in individual cages, and maintained on constant intraarterial infusion to assure catheter patency. Rats are permitted a 7-day postoperative recovery period to allow complete restoration of salt/water balance and body weight. Rats are assigned to vehicle or drug treatment groups (n=3/group). Drugs are uniformly suspended in 1% methylcellulose vehicle and given orally by gavage. Parameters are sampled continuously from the conscious, unrestrained rats and averaged every 15 min for the first 2 h and then hourly through 24 h after dosing. In order to take diurnal changes that are not drug related into account, 24 h timecourse curves for each parameter in drug treated SHR are compared to those from the concurrent control group. Since the average standard between-subject error is about 5 mm of mercury for arterial pressure parameters and about 11 bpm for heart rate, differences from concurrent control of greater than 10 mm of mercury and 22 bpm (2 SEM) are considered drug-related activity. Onset and duration are calculated from any pattern that achieves a maximum difference that meets these criteria.

To prepare the pharmaceutical compositions of this invention, one or more compounds or salts thereof of the invention, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 50 to about 100 mg of the active ingredient, although other unit dosages may be employed.

In therapeutic use as an antipsychotic agent, the compounds of this invention may be administered in an amount of from about 0.5 to 5 mg/kg per day, and more preferably 1–3 mg/kg per day. The dosages, however may be varied depending upon the requirements of the patient, the severity of the condition being treated, and the compound being employed. Determination of optimum dosages for a particular situation is within the skill of the art.

The following Examples illustrate the present invention, but are not deemed to be limiting. Examples 1, 6, and 10–19 describe the preparation of specific compounds listed in the Tables which follow the Examples, whereas the other Examples describe the preparation of intermediates described in the reaction schemes.

SPECIFIC EXAMPLES

EXAMPLE 1

1-[3-[[4-[2-(1-Methylethoxy)phenyl]-1-piperazinyl]methyl]benzoyl]piperidine Hydrochloride (3:2) (CP #53)

A solution of 3-(chloromethyl)benzoyl chloride (6 mL, 42.3 mmol) in 70 mL of THF was treated with diisopropylethylamine (33.1 mL, 0.19 mol). This solution was cooled in an acetone/dry ice bath and treated with piperidine (4.18 mL, 42.3 mmol) over a period of 2 min. After 5 min, the ice bath was removed, and the solution was allowed to warm to ambient temperature. After a total of 1 h, N-(2-isopropoxyphenyl)piperazine fumarate (14.45 g, 43 mmol) was added. The solution was stirred at ambient temperature overnight, and then at reflux for 7 h. The solution was allowed to cool to ambient temperature, then treated with water and methylene chloride. The organic layer was withdrawn, dried ($MgSO_4$), and filtered. The product was purified on silica gel (EtOAc/hexane, 6:4), dissolved in iPrOH, treated with concentrated HCl (ca. 2.5 mL), and then triturated with ethyl ether. The resultant solid was recrystallized from iPrOH/ethyl ether to give 9.1 g (45%) white powder, mp 222°–227° C. The $^1H$ NMR in $CDCl_3$ supported the assigned structure.

Elemental Analysis: Calculated for $C_{26}H_{35}N_3O_2 \cdot 1.5HCl$: C, 65.57; H, 7.72; N, 8.82; Cl, 11.17. Found: C, 65.77; H, 7.89; N, 8.78; Cl, 11.07.

Compound #2–16, 18–23, 25–27, 29–44, 46–65, 68–72, 74–85, 87–96, and 98 were prepared by the use of the general method described for Example 1 or slight alterations of it, with the necessary modifications in the choice of the initial amine starting material, (3-chloromethyl)benzoyl chloride, and aryl piperazine or aryl piperidine. Specifically, compound #2 was prepared by replacing piperidine with a mixture of cis and trans 2,5-dimethylpyrrolidine. The synthesis for compound #3 involved replacing N-(2-isopropoxyphenyl)piperazine (IPP) with N-(2-cyanophenyl)piperazine, and piperidine with cis-2,6-dimethylpiperidine. Compound #4 required a mixture of cis and trans (hexahydro)indoline instead of piperidine. The preparation of compound #5 used indoline instead of piperidine. Compound #6 required N-(2-pyrimidinyl)phenylpiperazine instead of IPP, 2-methoxy-5-(chloromethyl)benzoyl chloride instead of (3-cholomethyl)benzoyl chloride, and cis-2,6-dimethylpiperidine instead of piperidine. Compound #7 employed 2-nitro-5-(chloromethyl)benzoyl chloride instead of (3-chloromethyl)benzoyl chloride. Compound #8 employed N-(phenyl)-2-methylpiperazine in the place of IPP. The preparation of compounds #9–11 used N-(2-fluorophenyl)-2-methylpiperazine, N-(2-fluorophenyl)-cis-2,5-dimethylpiperazine, and N-(2-pyrimidinyl)piperazine, respectively, in the place of IPP and cis-2,6-dimethylpiperidine in the place of piperidine. The synthesis of compounds #12 and 13 used 2,2,6,6-(tetramethyl)piperidine and (S)-2-(benzyloxycarbonyl)pyrrolidine, respectively, instead of piperidine. Compound #14 employed N-(3,4-dichlorophenyl)piperazine instead of IPP and cis-2,6-dimethylpiperidine instead of piperidine. The preparation of compound #15 used 4-[2-(isopropoxy)phenyl]piperidine (XVII) instead of IPP, 2-methoxy-5-(chloromethyl)benzoyl chloride instead of (3-chloromethyl)benzoyl chloride, and cis-2,6-dimethylpiperidine instead of piperidine. Compound #16 required (S)-2-(hydroxymethyl)pyrrolidine instead of piperidine. Compound #18 required N-(2-methylphenyl)piperazine instead of IPP and 2-carbethoxypiperidine instead of piperidine. The synthesis of compound #19 employed 2-carbethoxypiperidine instead of piperidine. The preparation of compound #20 used N-(2-pyrimidinyl)piperazine in the place of IPP and (S)-2-(hydroxymethyl)pyrrolidine in the place of piperidine. The synthesis of compound #21 required the use of 2-(hydroxymethyl)piperidine instead of piperidine. Compound #22 was synthesized using N-(2-fluorophenyl)piperazine instead of IPP. Compound #23 was prepared using N-(2-pyrimidinyl)piperazine in the place of IPP and indoline in the place of piperidine. Compound #26 was prepared using 2-(hydroxymethyl)pyrrolidine in place of piperidine. Compound #27 was synthesized with N-[2-[MeCH(OH)CH$_2$O]Ph]piperazine in the place of piperidine. Compound #29 was prepared by replacing (3-chloromethyl)benzoyl chloride with 2-methoxy-5-(chloromethyl)benzoyl chloride. Compound #30 required the use of 7-(N-piperazinyl)benzofuran instead of IPP. Compound #31 required the use of 7-(N-piperazinyl)benzofuran and homopiperidine instead of IPP and piperidine. Compound #32 used 3-(N-piperazinyl)benzothiazole instead of IPP. The preparation of compound #33 entailed the use of 5-(N-piperazinyl)benzodioxane instead of IPP. The synthesis of compound #34 required the use of 5-(N-piperazinyl)benzodioxane instead of IPP and homopiperidine instead of piperidine. Compound #35 was synthesized with 1-(N-piperazinyl)naphthalene instead of IPP. Compound #36 required N-[3,4-(methylenedioxy)phenyl]piperazine instead of IPP. The preparation of compound #37 used 2-(N-piperazinyl)pyrimidine instead of IPP. Compound #38 required the use of XVII instead of IPP. Compound #39 required the use of XVII instead of IPP and homopiperidine instead of piperidine. Compound #40 required the use of XVII instead of IPP and cis-2,6-dimethylpiperidine instead of piperidine. Compound #41 required the use of XVII instead of IPP and morpholine instead of piperidine. Compound #42 required the use of 4-carbethoxypiperidine instead of piperidine. Compound #43 required the use of N-(methyl)phenethylamine instead of piperidine. Compound #45 required the use of 1,4-dioxa-8-azaspiro[4.5]decane instead of piperidine. Compound #46 required the use of N-(2,5-dimethoxyphenyl)piperazine instead of IPP. Compound #47 required the use of N-(2,5-dimethoxyphenyl)piperazine instead of IPP, and pyrrolidine instead of piperidine. Compound #48 required the use of N-(2,6-dimethoxyphenyl)piperazine. instead of IPP. Compound #49 required the use of N-(3-nitrophenyl)piperazine instead of IPP. Compound #50 required the use of IPP instead of piperidine. Compounds #51, 52, 54, 55, and 56 required the replacement of piperidine with azacyclobutane, pyrrolidine, homopiperidine, azacyclooctane, and morpholine respectively. Compounds #57, 58, 59, 60, and 61 required the replacement of piperidine with 3,3-dimethylpiperidine, 4-methylpiperidine, cis-2,6-dimethylpiperidine, 1,2,3,4-tetrahydro-6,7-(dimethoxy)isoquinoline, and a mixture of cis and trans perhydroisoquinoline respectively. Compounds #62, 63, and 64 required the replacement of piperidine with N-(phenyl)piperazine, N-(carbethoxy)piperazine, and N-(benzyl)piperazine respectively. Compound #65 required the use of N-(3-trifluoromethylphenyl)piperazine instead of both IPP and piperidine. Compounds #68, 69, 70, 71, and 72 required the replacement of piperidine with diethylamine, dibutylamine, N-(methyl)butylamine, cyclohexylamine, and N-(methyl)cyclohexylamine respectively. Compounds #74, 75, 76, and 77 required the replacement of piperidine with N-(methyl)benzylamine, 4-fluoroaniline, 2-aminomethyl-N-ethylpyrrolidine, and ammonia respectively. Compound #78 required the use of XXI instead of IPP. Compound #79 required the use of XXI instead of IPP and homopiperidine instead of piperidine. Compound #80 required the use of XXI instead of IPP and morpholine instead of piperidine. Compound #81 required the use of N-(2-propylphenyl)piperazine instead of IPP. Compound #82 required the use of N-(2-propylphenyl)piperazine instead of IPP and homopiperidine instead of piperidine. Compound #83 required the use of N-(2-ethoxyphenyl)piperazine instead of IPP and homopiperidine instead of piperidine. Compound #84 required the use of N-(2-methoxyphenyl)piperazine instead of IPP. Compound #85 required the use of N-(2-methoxyphenyl)piperazine instead of IPP and homopiperidine instead of piperidine. Compounds #87, 88, 89, 90, 91, and 92 required the replacement of IPP with N-(4-chlorophenyl)piperazine, N-(2-trifluoromethylphenyl)piperazine, N-(2-chlorophenyl)piperazine, N-(2-cyanophenyl)piperazine, N-(3-chlorophenyl)piperazine, and N-(3-trifluoromethylphenyl)piperazine respectively. Compound #93 required the use of N-(2-chlorophenyl)piperazine instead of IPP and homopiperidine instead of piperidine. Compounds #94 and 95 required the replacement of IPP with N-(3,5-dichlorophenyl)piperazine and phenylpiperazine respectively. Compounds #96 and 98 required the replacement of piperidine with 3-azabicyclo[3.2.2]nonane and N-(t-butyloxycarbonyl)-1,6-diaminohexane respectively.

In addition, compound #24 was prepared from compound #19 by a standard saponification reaction for the hydrolysis of an ester. Compound #97 was prepared from compound #98 by treatment with p-toluenesulfonic acid in methanol in a standard solvolysis reaction for removal of the t-butyloxycarbonyl group. In a similar manner, compound #44 was prepared by acidic solvolytic removal of the ketal group of compound #45. Compound #17 was prepared by a standard reduction reaction of the aromatic nitro group of compound #7. Additionally, compound #28 was synthesized by a standard acylation of the aromatic amine of compound #17.

EXAMPLE 2

1-Bromo-2-(1-methylethoxy)benzene (XIV)

A mixture of 2-bromophenol (23.2 mL, 0.20 mol), potassium carbonate (33.2 g, 0.24 mol) and 2-bromopropane (28.0 mL, 0.30 mol) in dimethylformamide (200 mL) was stirred in a preheated oil bath (60° C.) for 5 h. The cooled reaction mixture was then partitioned between ether and water. The layers were separated and the aqueous phase was extracted with ether. The combined organic solution was washed with copious amounts of water, 3N aqueous NaOH, dried (MgSO$_4$), filtered and concentrated in vacuo to furnish 39.3 g (91%) of XIV as a pale yellow oil which was carried on without further purification. The structure was supported by GC/MS and 90 MHz $^1$H NMR.

EXAMPLE 3

1-Carbethoxy-4-[2-(1-methylethoxy)phenyl]-4-piperidinol (XV)

To a suspended solution of Mg chips (10.07 g, 0.414 mol) in anhydrous ether (150 mL) at 22° C. under argon was added ca. 0.15 mL of 1,2-dibromoethane. Then 43.7 g (0.200 mol) of XIV in 200 mL of ether was added dropwise. After 50% of the aryl halide was added, the reaction began to reflux vigorously. The flask was cooled in an ice bath. After the refluxing had subsided somewhat, the ice bath was removed and the remaining aryl halide was added over a 1.5 h period. The resultant Grignard reagent was cooled in a dry ice/ether bath for 2 h and then treated with 34.0 mL (0.221 mol) of 98% 1-carbethoxy-4-piperidone. Upon complete addition of ketone, the reaction mixture was allowed to warm to 22° C. and stirred for 2 h. The reaction was then quenched with cold aqueous ammonium chloride which resulted in an emulsion. Addition of 1M aqueous HCl solution separated the two layers. The aqueous phase was extracted with additional ether and the combined organic solution was washed with 10% aqueous sodium bisulfite, 1.0M HCl, saturated NaHCO$_3$, and dried (K$_2$CO$_3$). Filtration concentration yielded 56.36 g of XV as a yellow viscous oil which was carried on without further purification The structure of this oil was supported by $^1$H NMR.

EXAMPLE 4

1-(Carbethoxy-4-[2-(1-methylethoxy)phenyl]piperidine (XVI)

A crude solution of XV (36 g), 10% palladium on carbon (1.80 g), 5 mL of concentrated HCl and 125 mL of MeOH was shaken on a Parr apparatus under 55.5 psig of hydrogen at 22° C. for 3 d. The reaction was filtered over Celite, and concentrated to a residue. This material was partitioned between ether and water. The organic solution was dried (MgSO$_4$), filtered, and concentrated to yield 29.34 g of XVI as a light yellow oil which was carried forward without further purification. The structure was supported by MS and $^1$H NMR.

EXAMPLE 5

4-[2-(1-Methylethoxy)phenyl]piperidine hydrochloride (XVII)

A mixture of crude XVI (29.3 g) and sodium hydroxide pellets (6.12 g, 0.106 mol) in DMSO (100 mL) was stirred in a preheated oil bath at 100° C. for 4 d. The reaction mixture was then poured into water (200 mL) and the crude product was extracted into methylene chloride. The methylene chloride extracts were dried over MgSO$_4$, filtered and concentrated to afford 21.34 g of a crude dark brown oil. This oil was dissolved in 1N aqueous HCl solution and washed with ether. The acidic aqueous solution was basified with 3N NaOH and the product was extracted into methylene chloride. The combined methylene chloride extracts were dried (MgSO$_4$), filtered and concentrated to yield 13.34 g of a semi-solid. This material was dissolved in iPrOH and acidified to a pH of 3 with concentrated HCl. The acidified solution was diluted with ether resulting in precipitation of the monohydrochloride salt which was collected by filtration and dried under vacuum to provide 11.21 g of XVII as a beige powder. The structure was supported by MS.

EXAMPLE 6

1-[3-[[4-[2-(1-Methylethoxy)phenyl]-1-piperidinyl]methyl]benzoyl]piperidine hydrochloride (CP #38)

A suspended mixture of XVII (3.75 g, 0.0146 mol), N-[3-(chloromethyl)benzoyl]pipridine (3.45 g, 0.0145 mol) and triethylamine (4.50 mL, 0.0322 mol) in N-methylpyrrolidinone (15 mL) was stirred in a preheated oil bath (80° C.) for 18 h. The reaction mixture was partitioned between methylene chloride and water. The phases were separated. The organic layer was washed with copious amounts of water, dried (MgSO$_4$), filtered and concentrated to afford 5.90 g of a brown oil. Flash chromatography of this material over silica gel using 4% MeOH in chloroform, and conversion to its corresponding HCl salt provided 2.66 g of CP #38 as off-white needles. The structure was supported by $^1$H NMR, MS, and IR.

Elemental Analysis. Calculated for C$_{27}$H$_{36}$N$_2$O$_2$.HCl: C, 70.95; H, 8.16; N, 6.13; Cl, 7.76. Found: C, 70.69; H, 7.91; N, 5.71; Cl, 7.70.

EXAMPLE 7

4-Fluoro-1-methylethoxy-1-nitrobenzene (XIX)

A suspended orange mixture of 5-fluoro-2-nitrophenol (XVIII, 10.0 g, 63.6 mmol), potassium carbonate (8.84 g, 64.0 mmol) and 2-bromopropane (6.00 mL, 63.6 mmol) in dimethylformamide (63.0 mL) was stirred at 22° C. under argon. After 1 d, an additional 2.0 mL of 2-bromopropane was added and the resultant mixture was heated at 60° C. for 1 do The reaction mixture was then partitioned between methylene chloride and 3N NaOH. The organic layer was separated and the basic aqueous layer was extracted with additional methylene chloride. The combined organic solution was washed with water (5×200 mL), dried ($MgSO_4$), filtered and concentrated to provide 12.02 g (95%) of an orange oil, 95% pure by GC, which was carried on without further purification. The structure was supported by MS and 90 MHz $^1H$ NMR.

EXAMPLE 8

4-Fluoro-2-methylethoxyaniline (XX)

A solution of XIX, (9.50 g, 45.3 mmol) and 10% palladium on carbon (0.50 g) in absolute ethanol (100 mL) was shaken on a Parr apparatus under 53 psi of hydrogen at 22° C. for 2 h. The reaction was filtered over Celite, diluted with chloroform, added ($MgSO_4$), filtered and concentrated to afford 8.37 g of a purple oil, 97% pure by GC, which was carried on without further purification. The structure was supported by GC/MS and $^1H$ NMR.

EXAMPLE 9

1-(4-Fluoro-2-methylethoxyphenyl)piperazine (XXI)

A crude solution of XX (8.35 g, 47.9 mmol), bis-(2-choroethyl)amine hydrochloride (12.83 g, 71.9 mmol) and triethylamine (10.00 mL, 71.7 mmol) in chlorobenzene (70 mL) was heated at reflux for 25 h. The dark brown reaction mixture was then partitioned between 3N NaOH and methylene chloride. The organic layer was separated, dried ($MgSO_4$), filtered and concentrated to yield 15.9 g of a brown oil. This crude free base was dissolved in MeOH, treated with fumaric acid (5.25 g), and diluted with ether. The monofumarate salt precipitated and was collected by filtration and dried in a vacuum oven at 60° C. to furnish 11.38 g of a brown solid, which was carried on without further purification. The structure was supported by MS and 90 MHz $^1H$ NMR.

EXAMPLE 10

1-[3-[[4-[2-(1-Methylethoxy)phenyl]-1-piperazinyl]methyl]benzoyl]-2-peridone Flumarate (CP ∩66)

A solution of 2-piperidinone (10.0 g, 0.101 mol), pyridine (16.35 g, 0.207 mol), and benzene (300 mL) was cooled in an ice bath and treated dropwise over 5 min with a solution of 3-(chloromethyl)benzoyl chloride (19.2 g, 0.102 mol). The resulting solution was stirred overnight at ambient temperature. Water (300 mL) was then added. The organic layer was separated, washed with 1N HCl (200 mL) and three 200 mL portions of water, dried ($NaSO_4$), filtered, and concentrated to give 16.5 g of a yellow oil. Addition of ether with cooling afforded 7.25 g of a cream-colored crystalline solid. The $^1H$ NMR was consistent with the desired structure.

A mixture of the intermediate prepared above (6.25 g, 0.025 mol), N-(2-methylethoxyphenyl)piperazine fumarate (8.40 g, 0.025 mol), potassium iodide (4.50 g, 0.027 mol), triethylamine (9.57 g, 0.095 mol) and N-methyl-2-pyrrolidinone (50 mL) was stirred for 5.5 h at ambient temperature, treated with water (250 mL), and extracted into ethyl ether (100 mL). The organic layer was separated, added ($NaSO_4$), filtered, and concentrated to give 6.3 g of an orange oil. This material was purified on 200 g of flash silica gel (EtOAc/methylene chloride, 1:1) to give 3.40 g of CP #66 as a clear oil. Treatment of the oil with fumaric acid (0.90 g) in iPrOH (20 mL) gave a white solid which was recrystallized from iPrOH to give 1.80 g (13%) of CP #66 as a white powder, mp 131.5°–133° C. The $^1H$ NMR in DMSO-$d_6$ was consistent with the assigned structure assigned structure.

Elemental Analysis. Calculated for $C_{26}H_{33}N_3O_3 \cdot C_4H_4O_4$: C, 65.32; H, 6.76; N, 7.62. Found: C, 65.28; H, 6.87; N, 7.41

In a similar manner, compounds #67, 73, and 86 were prepared by variation of the amide staring material or the aryl piperazine component of the reaction. Specifically, the preparation of compound #67 required the use of 2-azacyclooctanone instead of piperidinone. Compound #73 required the use of N-(methyl)acetamide instead of piperidinone. Compound #86 required the use of N-(2-methoxyphenyl)piperazine instead of IPP and 2-azacyclooctanone instead of piperidinone.

EXAMPLE 11

1-[4-[[4-[2-(1-Methylethoxy)phenyl]-1-piperazinyl]methyl]benzoyl]piperidine Dihydrochloride (CP #103)

A solution of 20 g of N-(2-methylethoxyphenyl)piperazine fumarate was partitioned between aqueous NaOH and methylene chloride. The organic layer was withdrawn and the aqueous layer was washed thrice more with methylene chloride. The organic layers were added ($MgSO_4$), filtered and concentrated to give 12.5 g of the free base of the piperazine, pure by TLC. This oil was treated with THF (100 mL), 4-bromobenzyl bromide (16.3 g, 65.3 mmol) and triethylamine (9.1 mL, 65.3 mmol). The solution was stirred at ambient temperature overnight, treated with EtOAc, washed with water, then the product was extracted into 1N HCl (3 times), hexane being added to the organic layer to facilitate the extraction. The combined aqueous extracts were made basic (ca. pH 10, NaOH), and then the product was extracted into methylene chloride (twice), dried ($MgSO_4$), filtered and concentrated to give 20.5 g of a yellow oil (89%). Fast-atom-bombardment MS: m/e 389 (M+1).

A mixture of the oil prepared above (7 g, 18 mmol) and 5.36 mL (54 mmol) of piperidine was treated with $Cl_2Pd(PPh_3)_2$ (0.81 mmol, 4.5 mol %) and heated at 95°–105° C. under 1 atm. of CO for a period of 8 h. The mixture was then cooled and treated with water and methylene chloride. The organic layer was separated, dried ($MgSO_4$), filtered and concentrated to give an oil which was purified on two Waters Prep 500 HPLC columns (EtOAc/hexane; 45:55) resulting in 3.35 g yellow oil pure by TLC. This oil was dissolved in iPrOH, filtered through a Millipore filter, treated with concentrated aqueous HCl (1.5 mL), and then triturated with ether. The resulting white solid precipitate was recrystallized from methylene chloride/ether, dried overnight at 70° C. under vacuum producing 2.9 g (32%) of CP #103 as a white powder, mp 205°–208° C. The $^1H$ NMR in $CDCl_3$ supported the assigned structure.

Elemental Analysis Calculated for $C_{26}H_{35}N_3O_2 \cdot 2HCl \cdot 0.25H_2O$: C, 62.59; H, 7.51; N, 8.42; Cl, 14.21; H$_2$O, 0.90. Found: C, 62.67; H, 7.83; N, 8.16; Cl, 13.87; H$_2$O, 2.82.

In a similar manner, compound #99 was prepared by using 4-bromophenethyl bromide instead of 4-bromobenzyl bromide in the reaction sequence.

EXAMPLE 12

1-[2-[[4-[2-(1-Methylethoxy)phenyl]-1-piperazinyl]methyl]benzoyl]piperidine Dihydrochloride (CP #111)

A solution of 2-(bromomethyl)benzoyl bromide (12.03 g, 43.28 mmol) in THF (100 mL) was cooled to −78° C. under nitrogen. The solution was treated with piperidine (4.28 mL, 43.3 mmol) and triethylamine (27.2 mL, 195 mmol). This caused a considerable white precipitate to form. The solution was allowed to slowly warm. When the temperature of the solution was ca. 0° C., N-(2-methylethoxyphenyl)piperazine fumarate (27.2 mL, 195 mmol) was added. The solution was warmed in an oil bath at 70° C. for 1 h. The mixture was then treated with water and methylene chloride. The methylene chloride layer was separated, dried (MgSO$_4$), filtered and concentrated to give 24 g of a brown oil. The oil was purified by high-pressure liquid chromatography (hexane/Et$_3$N, 9:1). This solvent system gave a fraction which contained 2.5 g of product highly pure by TLC. This was dissolved in iPrOH, filtered through a Millipore filter, and treated with concentrated aqueous HCl (1.13 mL), and the product was triturated with ether. The resultant solid was recrystallized from iPrOH/ether to give 1.7 g of CP #111 as a white powder (8%), mp 192.5°–196° C. Theill NMR in DMSO-d$_6$ was consistent with the assigned structure.

Elemental Analysis: Calculated for C$_{26}$H$_{35}$N$_3$O$_2$2.HCl: C, 63.15; H, 7.54; N, 8.50; Cl, 14.34. Found: C, 63.16; H, 7.65; N, 8.63; Cl, 13.92.

In a similar manner, compounds #108–110, 112, and 113 were prepared by variation of the initial amine component in the reaction sequence. Specifically, the preparation of compounds #108, 109, 110, 112 and 113 required the replacement of piperidine with 4-(carbethoxy)piperidine, 3,3-(dimethyl)piperidine, morpholine, N-(methyl)cyclopentylamine, and homopiperidine respectively.

EXAMPLE 13

1-[3-[[4[2-(1-Methylethoxy)phenyl]-1-piperazinyl]methyl]phenylsulfonyl]-4-ydroxypiperidine (CP #107)

N-Bromosuccinimide (6.27 g, 0.035 mole), m-toluenesulfonyl chloride (6.72 g, 0.035 mole), and benzoyl peroxide (0.67 g, 0.0019 mole) were combined in CCl$_4$ (40 mL) and heated at reflux 2 h. The reaction mixture was filtered and washed with CCl$_4$. The filtrate was concentrated to give m-bromomethylbenzenesulfonyl chloride, 9.74 g, as a viscous yellow oil.

A mixture of m-bromomethylbenzenesulfonyl chloride (2.50 g, 0.0093 mole), aqueous saturated sodium bicarbonate solution (10 mL), and methylene chloride (20 mL) was cooled to 0°–5° C. in an ice-water bath and treated with a solution of 4-hydroxypiperidine (0.99 g, 0.0097 mole) in methylene chloride (20 mL). The resulting mixture was stirred at 0° C. for 1 hour, warmed to room temperature, and stirred overnight. The organic layer was separated and the aqueous layer was extracted with methylene chloride. The organic layers were combined, washed with saturated sodium chloride solution, and dried over anhydrous magnesium sulfate. Filtration and evaporation afforded 3.16 g of oil. A solution of this material, N-(2-isopropoxyphenyl)piperazine (2.14 g, 0.0097 mole), N,N-diisopropylethylamine (1.32 g, 1.78 mL, 0.01 mol), and THF (40 mL) was heated to reflux under argon for 12 h, cooled, and evaporated. The residue was partitioned between methylene chloride and 3N sodium hydroxide solution and the organic layer was separated. Drying over anhydrous magnesium sulfate and evaporation afforded an oil which was purified by chromatography on flash silica, using methanol:ethanol:methylene chloride (1:1:98) as an eluant, to give 1-[3-[[4[2-(1-methylethoxy)phenyl]-1-piperazinyl]methyl]phenyl sulfonyl]-4-hydroxypiperidine (CP #107). This material was dissolved in diethyl ether and added to a solution of anhydrous hydrochloric acid and diethyl ether. The resulting slurry was filtered, washed with diethyl ether, and stirred in THF for 1.5 hours. Filtration and drying at 65° C. in vacuo afforded 1.90 g (33%) of the hydrochloride salt, m.p. 127°–130° C., whose structure was supported by $^1$H NMR and MS.

Elemental Analysis: Calculated for C$_{25}$H$_{35}$N$_3$O$_4$.2HCl-H$_2$O.0.75 tetrahydrofuranoate: C, 54.36; H, 7.33; N, 6.79; H$_2$O, 2.90. Found: C, 54.45; H, 7.53; N, 6.45; H$_2$O, 2.97.

EXAMPLE 14

1-[3-[[4-[2-(1-Methylethoxy)phenyl]-1-piperazinyl]methyl]thiobenzoyl]piperidine Hydrochloride (CP #1)

A solution of 1-[3-[[4-[2-(1-methylethoxy)phenyl]-1-piperazinyl]methyl]benzoyl]piperidine (CP #36, 3.86 g, 0.0092 mol) and toluene (50 mL) was treated with 2,4-bis(4-methoxyphenyl)-1,3-dithia-2,4-diphosphetane-2,4-disulfide (2.22 g, 0.0055 mole) and the resulting mixture was heated at 90° C. for 1 h. The reaction was cooled followed by the addition of toluene (50 mL), and mixed thoroughly with excess 3N sodium hydroxide solution. The organic layer was separated, washed with saturated sodium chloride solution, dried over anhydrous magnesium sulfate, and concentrated to an oily residue. Chromatography of this material on flash silica, using 1.5–2.5% methanol in methylene chloride, afforded CP #1 which was converted to its hydrochloride salt in ethereal hydrochloric acid, 3.61 g (77%), m.p. 221°–224° C. (dec, uncorrected). The structural assignment was supported by $^1$H NMR, chemical-ionization MS, and IR data.

Elemental Analysis: Calculated for C$_{26}$H$_{35}$N$_3$OS.HCl: C, 61.60; H, 7.30; N, 8.23. Found: C, 61.48; H, 7.47; N, 8.28.

EXAMPLE 15

1-[4-[2-[4-[2-(1-Methylethoxy)phenyl]-1-piperazinyl]ethyl]benzoyl]piperidine oxalate (CP #99)

The free base of 2-isopropoxyphenyl piperazine was prepared by treatment of the fumarate salt with aqueous bicarbonate followed by extraction into chloroform to provide a brown oil (30.6 g, 139 mmol) which was dissolved in 200 mL of anhydrous DMSO. To this solution was added 4-bromophenethyl bromide (44.0 g, 167 mmol), sodium iodide (4.85 g, 37.5 mmol) and N,N-diisopropylethylamine (73.6 g, 570 mmol). This solution was stirred under argon for 3 days. The reaction mixture was then poured into saturated aqueous bicarbonate solution which was extracted several times with ether. The ether extracts were combined, washed successively with aqueous bicarbonate solution and brine, dried (MgSO$_4$), and concentrated to provide a sticky brown solid. This material was purified on a Waters Delta Prep 3000 LC apparatus (35% hexanes-dichloromethane to pure dichloromethane) to afford 34.9 g (62%) of the desired aralkylpiperazine as a light brown solid. A mixture of this material (5.0 g, 12.4 mmol), piperidine (3.17 g, 37.2 mmol), and Cl$_2$Pd(PPh$_3$)$_2$ (0.39 g, 0.558 mmol) under 1 atmosphere of carbon monoxide was heated at 100° C. for 3 days. TLC analysis indicated ca. 40% conversion to a new product. An additional 0.39 g of palladium catalyst was added to the reaction mixture which was heated an additional 4 days. The reaction mixture was cooled, and to the resultant black solid was added chloroform and water. The layers were separated, and the aqueous layer was extracted with chloroform several times. The chloroform extracts were combined, dried (Na$_2$SO$_4$), and concentrated to provide a dark brown oil which was purified on flash silica gel (10% hexanes-chloroform to pure chloroform) to provide 1.13 g of pure 110 (free base) as a green solid. This material was dissolved in acetone, and oxalic acid (0.33 g) was added. When diethyl ether and hexanes were added, a cream-colored precipitate came out of solution. This solid was recrystallized from methanol/ether to provide 0.69 g (13%) of compound #99, mp 202°–205° C. The $^1$H NMR in DMSO-d$_6$ supported the assigned structure.

Elemental Analysis: Calculated for C$_{27}$H$_{37}$N$_3$O$_2$.1.1 C$_2$H$_2$O$_4$: C, 66.27; H, 7.48; N, 7.99. Found C, 66.00; H, 7.67; N, 7.84.

EXAMPLE 16

1-[4-[4-[4-[2-(1-Methylethoxy)phenyl]-1-piperazinyl]-4-oxobutyl]benzoyl]piperidine fumerate (CP #100)

The free base of 2-isopropoxyphenyl piperazine was prepared by treatment of the fumarate salt with aqueous bicarbonate followed by extraction into chloroform to provide a brown oil (41.0 g, 186 mmol) which was dissolved in 435 mL of anhydrous DMSO. To this solution was added 4'-bromo-4-chlorobutyrophenone (58.4 g, 223 mmol), sodium iodide (6.49 g, 50.2 mmol) and N,N-diisopropylethylamine (98.6 g, 763 mmol). This solution was stirred under argon for 7 days. The reaction mixture was poured into saturated aqueous bicarbonate solution which was extracted several times with ether. The ether extracts were combined, washed successively with aqueous bicarbonate solution and brine, dried (MgSO$_4$), and concentrated to provide a sticky brown solid. This material was purified on a Waters Delta Prep 3000 LC apparatus (45% hexanes-dichloromethane to pure dichloromethane) to afford 19.0 g (23%) of the desired halobutyophenone piperazine as a light brown solid. A mixture of this material (5.0 g, 11.2 mmol), piperidine (2.87 g, 33.7 mmol), and Cl$_2$Pd(PPh$_3$)$_2$ (0.35 g, 0.505 mmol) under 1 atmosphere of carbon monoxide was heated at 100° C. for 20 h. TLC analysis indicated ca. 60% conversion to a new product. An additional 0.35 g of palladium catalyst was added to the reaction mixture which was heated an additional 20 h. The reaction mixture was cooled, and to the resultant black solid was added chloroform and water. The layers were separated, and the aqueous layer was extracted with chloroform several times. The chloroform extracts were combined, dried (Na$_2$SO$_4$), and concentrated to provide a dark brown oil which was purified on flash silica gel (chloroform to 1% methanolchloroform) to give 1.25 g of pure free base of product as a golden brown oil (compound #100 free base). This material was dissolved in acetone and fumaric acid (0.30 g) was added. When diethyl ether and hexanes were added, a fluffy white precipitate came out of solution. This solid was recrystallized from acetone/ether to provide 0.74 g (11%) of the aryl piperazine oxobutylbenzamide #100, mp 154°–155.5° C. The $^1$H NMR in DMSO-d$_6$ supported the assigned structure.

Elemental Analysis: Calculated for C$_{29}$H$_{39}$N$_3$O$_3$1.1 C$_4$H$_4$O$_4$: C, 66.27; H, 7.23; N, 5.31. Found C, 66.26; H, 7.09; N, 6.77.

EXAMPLE 17

1-[4-[4-[4-[2-(1-Methylethoxy)phenyl]-1-piperinyl]-4-hydroxybutyl]benzoyl]piperidine bisoxalate (CP #101)

To a solution of compound 100 (4.98 g, 10.4 mmol) described above in 200 mL of absolute ethanol was added sodium borohydride (0.47 g, 12.5 mmol). The reaction mixture was stirred for 20 h under argon and then was cooled in ice. Cold 1N hydrochloric acid (20 mL) was added dropwise, and the reaction mixture was stirred for 1 min and then was basified with solid potassium carbonate. The resulting mixture was extracted with chloroform. The chloroform extracts were combined, dried (Na$_2$SO$_4$), and concentrated to provide a green foam which was purified on flash silica gel (1% methanol-chloroform to 5% methanol-chloroform to give 1.25 g of pure alcohol as a yellow foam. This compound was dissolved in hot methanol, and oxalic acid (0.33 g) was added. When ether and hexanes were added, a white precipitaate formed. This solid was recrystallized from methanol/ether to afford 0.44 g (9%) of the compound 101, mp 141°–144.5° C. The $^1$H NMR in DMSO-d$_6$ supported the assigned structure.

Elemental Analysis: Calculated for C$_{29}$H$_{41}$N$_3$O$_3$.2 C$_2$H$_2$O$_4$: C, 60.08; H, 6.88; N, 6.37. Found C, 60.32; H, 6.99; N, 6.56.

EXAMPLE 18

1-[4-[4-[4-[2-(1-Methylethoxy)phenyl]-1-piperazinyl]butyl]benzoyl]piperidine dihydromide (102)

A mixture of compound 101 (3.20 g, 6.67 mmol), 20% palladium hydroxide on charcoal (1.00 g), and concentrated hydrochloric acid (1.7 mL, 20.0 mmol) in 100 mL of 95% ethanol was combined in a Parr bottle. The mixture was shaken under 60 psi of hydrogen at 50° C. for 8 days. The reaction mixture was cooled and filtered through Dicalite. The filtrate was concentrated to provide an olive green foam. To this material was added saturated aqueous bicarbonate solution and chloroform. The resulting mixture was passed through Dicalite, and the layers were separated. The aqueous layer was extracted with chloroform. The chloroform extracts were combined, dried (Na$_2$SO$_4$), and concentrated to provide a light brown oil which was purified on flash silica gel (1% methanol-chloroform) to give 2.46 g of pure compound 102 (free base) as a golden brown oil. This compound was dissolved in hot methanol, and concentrated HBr (1.1 mL) was added. When ether and hexanes were added, a tan precipitate formed. This solid was recrystallized from methanol/ether to afford 1.36 g (32%) of compound 102, mp 197.5°–198.5° C. The $^1$H NMR in DMSO-d$_6$ supported the assigned structure.

Elemental Analysis: Calculated for C$_{29}$H$_{41}$N$_3$O$_2$.2.0HBr: C, 55.69; H, 6.93; N, 6.72; Br, 25.55. Found C, 55.44;H, 7.11; N, 6.49; Br, 24.68.

EXAMPLE 19

1-[3-[[4-[2-(1-Methylethoxy)phenyl]-1-piperazinyl]-1-ethyl]benzoyl]Oxalate Hydrate (CP #25)

A mixture of 1-[2-(methylethoxy)phenyl]piperazine (IPP, 7.28 g, 0.033 mol), 3-acetylbenzonitrile (4.80 g, 0.033 mol), and titanium isopropoxide (11.74 g, 0.041 mol) was stirred at room temperature for 2 h, heated to 80° C. for several minutes, and then cooled to room temperature. Methanol (150 mL) was added and the mixture was heated to dissolve most of the solids. After cooling to room temperature, sodium borohydride (2.27 g, 0.060 mol) was added in portions and the mixture was stirred overnight at room temperature. The reaction mixture was concentrated on a rotary evaporator and the residue was partitioned between 3N NaOH/$CH_2Cl_2$. The organic layer was separated, dried ($K_2CO_3$), filtered, and evaporated to an oily residue which was passed through flash grade silica using 4:1 hexane:EtOAc as eluant to give 3-[1-[4-[2-(1-methylethoxy)phenyl]-1-piperazinyl]ethyl]benzonitrile as an oil (1.55 g, 13.5%).

A solution of this material (1.55 g, 4.4 mmol), 10N NaOH (10 mL), and EtOH (10 mL) was refluxed for 8 h and stirred overnight at room temperature. The reaction was concentrated by evaporation and the residue was dissolved in water (50 mL). Addition of acetic acid (5 mL) caused a white precipitate to form which was filtered to give 3-[1-[4-[2-(1-methylethoxy)phenyl]-1-piperazinyl]ethyl]benzoic acid as a white solid, 1.26 g (77%).

This material was dissolved in DMF (11 mL) and treated portionwise at room temperature with 1,1'-carbonyldiimidazole (0.32 g, 0.002 mol). The reaction was stirred at room temperature for 1.5 h and then treated with piperidine (0.314 g, 3.7 mol). After stirring an additional 2 h, water (105 mL) was added and the mixture was extracted with ether. The ether layer was washed with saturated NaCl solution, separated, dried ($K_2CO_3$), filtered, and evaporated to give compound #25 (free base) as a yellow oil (0.60 g). This material was dissolved in EtOH and treated with oxalic acid (0.17 g, 0.0019 mol). Addition of ether caused a solid to precipitate which was collected by filtration, affording compound #25 (oxalate salt) as a white solid (0.123 g, 14%), m.p. 124°–130° C. H-1 NMR and mass spectral analysis supported the assigned structure.

Elemental Analysis: Calculated for $C_{27}H_{37}N_3O_2 \cdot C_2H_2O_4 \cdot H_2O$: C, 64.07; H, 7.60; N, 7.73; $H_2O$, 3.31. Found: C, 64.29; H, 7.37; N, 7.64; $H_2O$, 1.22.

TABLE 1

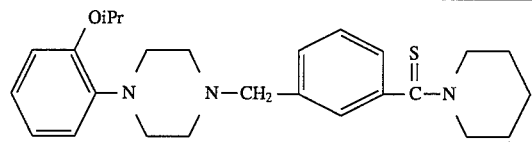

| Compound No. | CAR 5 mg/kg (Escape Loss) IP Administration | Salt Form[1] | M.p. (°C.) | Receptor Binding ($K_I$ nM) $D_2$ |
|---|---|---|---|---|
| 1 | −71%(20%) | HCl | 221–224 | 8.0 |

Note 1: Where solvates were identified by H-1 NMR analysis and elemental analysis in Tables 1–5, they are identical in parenthesis.

TABLE 2

| Comp'd | Ar | R¹ | R² | R³ | R⁵ | R⁸ | R⁹ | X | CAR 15 mg/kg (Escape Loss) IP Administration | Salt Form | M.p. (°C.) | Receptor Binding ($K_i$, nM) $D_2$ |
|---|---|---|---|---|---|---|---|---|---|---|---|---|
| 2 | 2-(OiPr)Ph | H | H | H | H | | 2,6-dimethylcyclohexyl | N | −92%(16%) | Maleate (0.5 hydrate) | 165–167 | 4.7 |
| 3 | 2-(CN)Ph | H | H | H | H | | 2,6-dimethylcyclohexyl | N | −63%(3%) | Maleate (0.5 hydrate) | 168.5–169.5 | 303 |
| 4 | 2-(OiPr)Ph | H | H | H | H | | decahydronaphthyl | N | −96%(33%) | 2 HBr (0.2 hydrate) | 199–201 | 5.6 |
| 5 | 2-(OiPr)Ph | H | H | H | H | | 1,2,3,4-tetrahydronaphthyl | N | −96%(29%) | Oxalate (0.1 hydrate) | 198–199 | >1000 |
| 6 | 2-Pyrimidinyl | H | H | H | MeO | | 2,6-dimethylcyclohexyl | N | −46%(4%) | — | 183–185 | 808 |
| 7 | 2-(OiPr)Ph | H | H | H | NO₂ | | —(CH₂)₅— | N | −23%(1%) | Fumarate | 151–153 | 85 |
| 8 | Ph | H | Me | H | H | | —(CH₂)₅— | N | −7%(1%) | HCl (0.75 hydrate) | 138–144 | >1000 |
| 9 | 2-FPh | Me | H | H | H | | 2,6-dimethylcyclohexyl | N | −22(0) | (0.5 hydrate) | — | 43 |

TABLE 2-continued

Structure:
$$\text{Ar-X} \begin{pmatrix} R^1 \\ R^2 \end{pmatrix} \text{N-CH}(R^3) - \text{Ar}(R^5) - \text{C(=O)-N}(R^8)(R^9)$$

| Comp'd | Ar | $R^1$ | $R^2$ | $R^3$ | $R^5$ | $R^8$ | $R^9$ | X | CAR 15 mg/kg (Escape Loss) IP Administration | Salt Form | M.p. (°C.) | Receptor Binding ($K_i$ nM) $D_2$ |
|---|---|---|---|---|---|---|---|---|---|---|---|---|
| 10 | 2-FPh | Me | Me | H | H | H | 2,6-dimethylcyclohexyl (Me, Me) | N | −13%(0) | Oxalate (hydrate) | 93–95 | 89 |
| 11 | 2-Pyridinyl | H | H | H | H | H | 2,6-dimethylcyclohexyl (Me, Me) | N | −34%(15%) | 1.5 Oxalate (0.5 hydrate) | 197.5–199.5 | 36 |
| 12 | 2-(OiPr)Ph | H | H | H | H | H | 2,2,6,6-tetramethylcyclohexyl (Me, Me, Me, Me) | N | −92%(9%) | Maleate | 167–168 | 4.7 |
| 13 | 2-(OiPr)Ph | H | H | H | H | H | cyclopentyl-CO₂Bn | N | −4%(0%) | Oxalate | 151–153 | 10 |
| 14 | 3,4-Cl₂Ph | H | H | H | H | H | 2,6-dimethylcyclohexyl (Me, Me) | N | −63%(3%) | Fumarate (0.5 hydrate) | 129–134 | 6.5 |
| 15 | 2-(OiPr)Ph | H | H | H | MeO | H | 2,6-dimethylcyclohexyl (Me, Me) | CH | −86%(30%) | — (0.1 CH₂Cl₂) | 50–60 | 43 |
| 16 | 2-(OiPr)Ph | H | H | H | H | H | cyclopentyl-CO₂H | N | −99%(35%) | Fumarate | 166–168 | 5.1 |
| 17 | 2-(OiPr)Ph | H | H | H | NH₂ | H | −(CH₂)₅− | N | −100%(87%) | HCl(0.25 hydrate) (0.67 methanolate) | 201–202 | 6.4 |

TABLE 2-continued

| Comp'd | Ar | $R^1$ | $R^2$ | $R^3$ | $R^5$ | $R^8$ | $R^9$ | X | CAR 15 mg/kg (Escape Loss) IP Administration | Salt Form | M.p. (°C.) | Receptor Binding ($K_i$ nM) $D_2$ |
|---|---|---|---|---|---|---|---|---|---|---|---|---|
| 18 | 2-MePh | H | H | H | H | H | cyclohexyl-CO$_2$Et | N | −24%(9%) | 2 HBr (hydrate) | 185–188 | 132 |
| 19 | 2-(OiPr)Ph | H | H | H | H | H | cyclohexyl-CO$_2$Et | N | −97%(46%) | 1.1 Oxalate | 138–156 | 4.1 |
| 20 | 2-Pyrimidinyl | H | H | H | H | H | cyclopentyl-CO$_2$H | N | −17%(1) | 0.9 Maleate | 177.5–180.5 | >1000 |
| 21 | 2-(OiPr)Ph | H | H | H | H | H | cyclohexyl-CO$_2$H | N | −99%(43%) | 1.1 Oxalate (0.5 hydrate) | 110–129 | 5.2 |
| 22 | 2-FPh | H | H | H | H | H | −(CH$_2$)$_5$− | N | −84%(21%) | Oxalate | 192.5–194.5 | 263 |
| 23 | 2-pyrimidinyl | H | H | H | H | H | 2-propylphenyl | N | −62%(9%) | Oxalate (0.14 hydrate) | 216–219 | >1000 |
| 24 | 2-(OiPr)Ph | H | H | H | H | H | cyclohexyl-CO$_2$H | N | Not Tested | Oxalate (0.7 hydrate) | 282.5–285.5 | >1000 |
| 25 | 2-(OiPr)Ph | H | H | Me | H | H | −(CH$_2$)$_5$− | N | Not Tested | Oxalate (hydrate) | 124–130 | 122 |

TABLE 2-continued

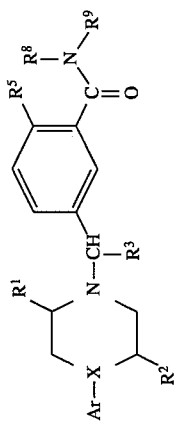

| Comp'd | Ar | R¹ | R² | R³ | R⁵ | R⁸ | R⁹ | X | CAR 15 mg/kg (Escape Loss) IP Administration | Salt Form | M.p. (°C.) | Receptor Binding ($K_I$, nM) $D_2$ |
|---|---|---|---|---|---|---|---|---|---|---|---|---|
| 26 | 2-(OiPr)Ph | H | H | H | H | H | CH₂OH-cyclopentyl | N | −100%(43%) | Fumarate | 171–175 | 9 |
| 27 | 2-[MeCH(OH)CH₂O]Ph | H | H | H | H | H | −(CH₂)₅− | N | −8%(0) | Oxalate (0.2 hydrate) | 184.5–187 | 703 |
| 28 | 2-(OiPr)Ph | H | H | H | AcNH | H | −(CH₂)₅− | N | −100%(17%) | 1.5 Fumarate (0.5 propanol, 1.5 hydrate) | 104–106.5 | 29 |
| 29 | 2-(OiPr)Ph | H | H | H | MeO | H | −(CH₂)₅− | N | −98%(50%) at 5 mg/kg | 2 Oxalate (0.75 hydrate) | 148–150 | 32 |
| 30 | 7-Benzofuranyl | H | H | H | H | H | −(CH₂)₅− | N | −82%(19%) at 5 mg/kg | HBr (hydrate) | 155–158 | 15 |
| 31 | 7-Benzofuranyl | H | H | H | H | H | −(CH₂)₆− | N | −81%(20%) at 5 mg/kg | HBr (0.5 hydrate) | 139–143 | 14 |
| 32 | benzisothiazolyl | H | H | H | H | H | −(CH₂)₅− | N | −90%(8%) | 1.1 HCl | 243.5–244 | 41 |
| 33 | 5-Benzodioxanyl | H | H | H | H | H | −(CH₂)₅− | N | −94%(8%) | 1.4 HClO₄ | 150–156 | >1000 |
| 34 | 5-Benzodioxanyl | H | H | H | H | H | −(CH₂)₆− | N | −98%(11%) | 1.2 HClO₄ | 134–136 | 127 |
| 35 | 1-Naphthyl | H | H | H | H | H | −(CH₂)₅− | N | −19%(0) at 15 mg/kg | 0.8 Maleate | 137–140 | 124 |
| 36 | methylenedioxyphenyl | H | H | H | H | H | −(CH₂)₅− | N | −10%(0) | Oxalate | 212–216 | >1000 |
| 37 | 2-Pyrimidinyl | H | H | H | H | H | −(CH₂)₅− | N | −18%(1%) | — | 107–108 | >1000 |
| 38 | 2-(OiPr)Ph | H | H | H | H | H | −(CH₂)₅− | CH | −92%(5%) | HCl | 190–193 | 2.8 |
| 39 | 2-(OiPr)Ph | H | H | H | H | H | −(CH₂)₆− | CH | −86%(2%) | HCl (0.75 hydrate) | 170–172 | 1.2 |

TABLE 2-continued

Structure:

Ar—X with R¹, R², and piperidine ring connected to N—CH(R³) linked to phenyl bearing R⁵ at ortho and C(=O)—N(R⁸)(R⁹) at meta position.

| Comp'd | Ar | R¹ | R² | R³ | R⁵ | R⁸ | R⁹ | X | CAR 15 mg/kg (Escape Loss) IP Administration | Salt Form | M.p. (°C.) | Receptor Binding ($K_i$ nM) $D_2$ |
|---|---|---|---|---|---|---|---|---|---|---|---|---|
| 40 | 2-(OiPr)Ph | H | H | H | H | H | Me-CH(CH₂)₃CH(Me)-CH₂- (2,6-dimethylheptyl-like) | CH | −98%(37%) | HCl (0.25 hydrate) | 165–167 | NT |
| 41 | 2-(OiPr)Ph | H | H | H | H | H | tetrahydropyran-4-yl | CH | −96%(70%) | HCl | 180–181 | 9.6 |
| 42 | 2-(OiPr)Ph | H | H | H | H | H | cyclohexyl-CO₂Et | N | −18%(0%) | 1.35 HCl | 210–212 | 121 |
| 43 | 2-(OiPr)Ph | H | H | H | H | Me | (CH₂)₂Ph | N | −77%(0%) at 15 mg/kg | Oxalate | 64–166 | 19 |
| 44 | 2-(OiPr)Ph | H | H | H | H | H | 4-oxocyclohexyl | N | −68%(16%) | — | 200–202 | 42 |
| 45 | 2-(OiPr)Ph | H | H | H | H | H | 1,4-dioxaspiro[4.5]dec-8-yl | N | −95%(20%) | — | 102.5–104.3 | 20 |
| 46 | 2,5-(MeO)₂Ph | H | H | H | H | H | —(CH₂)₅— | N | −66%(48%) | HCl | 200–201 | 592 |
| 47 | 2,5-(MeO)₂Ph | H | H | H | H | H | —(CH₂)₄— | N | 2%(0) at 15 mg/kg | HCl | 237–238 | >1000 |
| 48 | 2,6-(MeO)₂Ph | H | H | H | H | H | —(CH₂)₅— | N | −1%(1%) at 15 mg/kg | 1.8 HCl | 151–153 | >1000 |
| 49 | 3-NO₂ | H | H | H | H | H | —(CH₂)₅— | N | −78%(0) at 15 mg/kg | Fumarate | 194–197 | >1000 |

TABLE 2-continued

| Comp'd | Ar | R¹ | R² | R³ | R⁵ | R⁸ | R⁹ | X | CAR 15 mg/kg (Escape Loss) IP Administration | Salt Form | M.p. (°C.) | Receptor Binding ($K_i$ nM) $D_2$ |
|---|---|---|---|---|---|---|---|---|---|---|---|---|
| 50 | 2-(OiPr)Ph | H | H | H | H | H | 2-(iPrO)-N-piperidinyl-phenyl | N | 0%(1%) | 1.3 HCl (0.8 hydrate) | 197–199 | 171 |
| 51 | 2-(OiPr)Ph | H | H | H | H | H | $-(CH_2)_3-$ | N | −88%(0) at 15 mg/kg | Maleate | 122–124 | NT |
| 52 | 2-(OiPr)Ph | H | H | H | H | H | $-(CH_2)_4-$ | N | −98%(0%) at 7.5 mg/kg | 1.5 HCl | 197–199 | 35 |
| 53 | 2-(OiPr)Ph | H | H | H | H | H | $-(CH_2)_5-$ | N | −91%(8%) at 7.5 mg/kg | 1.5 HCl | 222–227 | 2.2 |
| 54 | 2-(OiPr)Ph | H | H | H | H | H | $-(CH_2)_6-$ | N | −88%(5%) | HCl | 212–214 | 6.3 |
| 55 | 2-(OiPr)Ph | H | H | H | H | H | $-(CH_2)_7-$ | N | −93%(27%) | Oxalate | 172–174 | 5.3 |
| 56 | 2-(OiPr)Ph | H | H | H | H | H | morpholinyl (O) | N | −68%(27%) | 1.85 HCl (hydrate) | 145–148 | 95 |
| 57 | 2-(OiPr)Ph | H | H | H | H | H | 1,1-dimethylcyclohexyl | N | −86%(25%) | Oxalate (0.2 hydrate) | 156–158 | 4.8 |
| 58 | 2-(OiPr)Ph | H | H | H | H | H | 2-methylcyclohexyl | N | −81%(9%) | Fumarate | 157–158.5 | 9 |
| 59 | 2-(OiPr)Ph | H | H | H | H | H | 2,6-dimethyl-hept-4-yl | N | −72%(10%) | HCl (0.5 hydrate) | 216–218 | 7.2 |

TABLE 2-continued

| Comp'd | Ar | R¹ | R² | R³ | R⁵ | R⁸ | R⁹ | X | CAR 15 mg/kg (Escape Loss) IP Administration | Salt Form | M.p. (°C.) | Receptor Binding ($K_i$, nM) $D_2$ |
|---|---|---|---|---|---|---|---|---|---|---|---|---|
| 60 | 2-(OiPr)Ph | H | H | H | H | H | 2,5-(OMe)$_2$-4-Et-phenyl | N | −93%(7%) at 15 mg/kg | Oxalate (0.4 hydrate) | 151–154 | 11 |
| 61 | 2-(OiPr)Ph | H | H | H | H | H | trans-decahydronaphthyl | N | −36%(3%) | Oxalate | 171–173 | 11.4 |
| 62 | 2-(OiPr)Ph | H | H | H | H | H | 4-Ph-piperidin-1-yl | N | −28%(23%) | 3 HCl | 229–231 | 10.4 |
| 63 | 2-(OiPr)Ph | H | H | H | H | H | 4-(CO$_2$Et)-piperidin-1-yl | N | −20%(1%) | 1.1 HCl | 205–207 | 121 |
| 64 | 2-(OiPr)Ph | H | H | H | H | H | 4-(CH$_2$Ph)-piperidin-1-yl | N | −23%(2%) at 30 mg/kg | 2.15 HCl | 262–263 | 40 |
| 65 | 2-(OiPr)Ph | H | H | H | H | H | 4-(3-CF$_3$-phenyl)-piperidin-1-yl | N | −7%(0) at 30 mg/kg | 2 HCl | 220–223 | ca. 1000 |

TABLE 2-continued

Structure: Ar—X with R¹, R² substituents on chain, N—CH(R³) linked to phenyl bearing R⁵ and C(=O)N(R⁸)R⁹ group.

| Comp'd | Ar | R¹ | R² | R³ | R⁵ | R⁸ | R⁹ | X | CAR 15 mg/kg (Escape Loss) IP Administration | Salt Form | M.p. (°C.) | Receptor Binding ($K_i$ nM) $D_2$ |
|---|---|---|---|---|---|---|---|---|---|---|---|---|
| 66 | 2-(OiPr)Ph | H | H | H | H | H | (cycloheptanone-2-yl) | N | −92%(0) at 15 mg/kg | Fumarate | 131.5–133 | 39 |
| 67 | 2-(OiPr)Ph | H | H | H | H | H | (cyclooctanone-2-yl) | N | −28%(7%) | Fumarate | 172–173 | 10.2 |
| 68 | 2-(OiPr)Ph | H | H | H | H | Et | Et | N | −96%(14%) | 1.5 HCl | 175.5–180 | 14 |
| 69 | 2-(OiPr)Ph | H | H | H | H | nBu | nBu | N | −6%(0%) at 15 mg/kg | 1.4 HCl | 163–167 | 16 |
| 70 | 2-(OiPr)Ph | H | H | H | H | nBu | Me | N | −68%(2%) | 1.05 HCl | 166–169 | 15 |
| 71 | 2-(OiPr)Ph | H | H | H | H | cC₆H₁₁ | H | N | −86%(0) at 15 mg/kg | 2 HCl | 170–175 | 47 |
| 72 | 2-(OiPr)Ph | H | H | H | H | cC₆H₁₁ | Me | N | −99%(21%) | Fumarate (hydrate) | 170–172.5 | 5.4 |
| 73 | 2-(OiPr)Ph | H | H | H | H | Ac | Me | N | −48%(22%) | Fumarate (isopropanol) | 159–161 | 158 |
| 74 | 2-(OiPr)Ph | H | H | H | H | Me | CH₂Ph | N | −23%(1%) | Oxalate | 160–162 | 13 |
| 75 | 2-(OiPr)Ph | H | H | H | H | 4-FPh | H | N | −1%(0) at 30 mg/kg | Oxalate | 149–151 | ca. 30 |
| 76 | 2-(OiPr)Ph | H | H | H | H | —CH₂-(1-Et-pyrrolidin-2-yl) | H | N | −75%(0) at 15 mg/kg | 2.6 HBr (1.5 hydrate, 0.5 EtOH) | 192–195 | 13.9 |
| 77 | 2-(OiPr)Ph | H | H | H | H | H | H | N | −89%(27%) | — | 172–175 | 46 |
| 78 | 2-(OiPr)-4-FPh | H | H | H | H | —(CH₂)₅— | | N | −82%(4%) | 1.5 HCl | 204–206.5 | 19 |
| 79 | 2-(OiPr)-4-FPh | H | H | H | H | —(CH₂)₆— | | N | −86%(44%) | HCl (0.25 hydrate) | 180–184 | 12 |

TABLE 2-continued

| Comp'd | Ar | $R^1$ | $R^2$ | $R^3$ | $R^5$ | $R^8$ | $R^9$ | X | CAR 15 mg/kg (Escape Loss) IP Administration | Salt Form | M.p. (°C.) | Receptor Binding ($K_I$ nM) $D_2$ |
|---|---|---|---|---|---|---|---|---|---|---|---|---|
| 80 | 2-(OiPr)—4-FPh | H | H | H | H | H | tetrahydropyranyl | N | −91%(14%) | HCl | 206–208 | 79 |
| 81 | 2-(nPr)Ph | H | H | H | H | H | −(CH$_2$)$_5$− | N | −8%(0) at 15 mg/kg | HCl | 190.5–192.5 | 38 |
| 82 | 2-(nPr)Ph | H | H | H | H | H | −(CH$_2$)$_6$− | N | −8%(0%) at 15 mg/kg | 1.4 HClO$_4$ (0.25 hydrate) | 157.5–160.5 | 41 |
| 83 | 2-(OEt)Ph | H | H | H | H | H | −(CH$_2$)$_6$− | N | −97%(26%) | HCl | 188–190 | 57 |
| 84 | 2-(OMe)Ph | H | H | H | H | H | −(CH$_2$)$_5$− | N | −98%(42%) | 2 HCl | 184–186 | 29 |
| 85 | 2-(OMe)Ph | H | H | H | H | H | −(CH$_2$)$_6$− | N | −95%(22%) | HCl (1.5 hydrate) | 196–198 | 201 |
| 86 | 2-(OMe)Ph | H | H | H | H | H | cyclooctanone | N | −27%(17%) at 15 mg/kg | 0.5 Fumarate (0.2 hydrate) | 112–155.5 | 121 |
| 87 | 4-ClPh | H | H | H | H | H | −(CH$_2$)$_5$− | N | −5%(0%) at 15 mg/kg | 2 HCl (hydrate) | 172–175 | >1000 |
| 88 | 2-(CF$_3$)Ph | H | H | H | H | H | −(CH$_2$)$_6$− | N | −60%(7%) at 15 mg/kg | 1.1 HCl | 210–211.5 | 281 |
| 89 | 2-ClPh | H | H | H | H | H | −(CH$_2$)$_5$− | N | −68%(0%) at 15 mg/kg | HCl | 170–174 | 77 |
| 90 | 2-CNPh | H | H | H | H | H | −(CH$_2$)$_5$− | N | −74%(5%) at 15 mg/kg | 0.85 Fumarate | 182–184 | 63 |
| 91 | 3-ClPh | H | H | H | H | H | −(CH$_2$)$_5$− | N | −36%(21%) at 15 mg/kg | HCl | 183–184 | 347 |
| 92 | 3-(CF$_3$)Ph | H | H | H | H | H | −(CH$_2$)$_5$− | N | −72%(3%) at 15 mg/kg | HCl | 207–209 | 682 |
| 93 | 2-ClPh | H | H | H | H | H | −(CH$_2$)$_6$− | N | −23%(0%) at 15 mg/kg | HClO$_4$ (0.3 hydrate) | 180–183.7 | 18 |
| 94 | 3,5-Cl$_2$Ph | H | H | H | H | H | −(CH$_2$)$_5$− | N | −43%(3%) | HCl (0.5 hydrate) | 242–248 | 21 |
| 95 | Ph | H | H | H | H | H | −(CH$_2$)$_5$− | N | −82%(11%) at 15 mg/kg | HCl | 134–136 | >1000 |

TABLE 2-continued

Structure:

Ar—X with piperidine ring bearing R¹, R² substituents, N—CH(R³) linked to phenyl with R⁵ and C(=O)N(R⁸)R⁹ groups.

| Comp'd | Ar | R¹ | R² | R³ | R⁵ | R⁸ | R⁹ | X | CAR 15 mg/kg (Escape Loss) IP Administration | Salt Form | M.p. (°C.) | Receptor Binding ($K_i$, nM) $D_2$ |
|---|---|---|---|---|---|---|---|---|---|---|---|---|
| 96 | 2-(OiPr)Ph | H | H | H | H | H | bicyclic | N | −98%(67%) at 15 mg/kg | 1.1 Oxalate (0.1 hydrate) | 162–165 | NT |
| 97 | 2-(OiPr)Ph | H | H | H | H | H | (CH$_2$)$_6$NH$_2$ | N | −99%(26%) at 15 mg/kg | 2 Oxalate (0.67 hydrate) | 134–136 | 15 |
| 98 | 2-(OiPr)Ph | H | H | H | H | H | (CH$_2$)$_6$NHBoc | N | −8%(0%) at 15 mg/kg | Oxalate | 131–133 | 88 |

TABLE 3

Structure: 2-OiPr-phenyl-N(piperazine)N-(CH₂)ₙ-C(R³)(R⁴)-(phenyl)-C(=O)-N(piperidine)

| Comp'd | R³ | R⁴ | n | CAR 15 mg/kg (Escape Loss) IP Administration | Salt Form | M.p. (°C.) | Receptor Binding ($K_I$ nM) $D_2$ |
|---|---|---|---|---|---|---|---|
| 99 | H | H | 1 | −92%(48%) | Oxalate | 202–205.5 | 24 |
| 100 | =O | | 3 | −97%(49%) | 1.1 Oxalate | 154–155.5 | 11 |
| 101 | H | OH | 3 | −78%(3%) | 2 Oxalate | 141–144.5 | 13 |
| 102 | H | H | 3 | Not tested | 2 HBr | 195.5–199.5 | 7.2 |
| 103 | H | H | 0 | −35%(6%) at 5 mg/kg | 2 HCl (0.25 hydrate) | 205–208 | ca. 100 |

TABLE 4

Structure: 2-OiPr-phenyl-N(piperazine)N-CH₂-(phenyl)-SO₂-N(R⁸)(R⁹)

| Comp'd | R⁸ | R⁹ | CAR 5 mg/kg (Escape Loss) IP Administration | Salt Form | M.p. (°C.) | Receptor Binding ($K_I$ nM) $D_2$ |
|---|---|---|---|---|---|---|
| 104 | 1-methyl-1-cyclohexyl (Me, Me) | | −4%(2%) | 2 HCl | 197–202 | 45 |
| 105 | −(CH₂)₅− | | −7%(0) | 2 HCl (hydrate) | 189–191 | 18 |
| 106 | −(CH₂)₄− | | −27%(0) | — | 113–115 | 196 |
| 107 | 4-hydroxycyclohexyl | | −95%(5%) | 2 HCl (hydrate) | 127–130 | 69 |

TABLE 5

Structure: 2-OiPr-phenyl-N(piperazine)N-CH₂-(phenyl)-C(=O)-N(R⁸)(R⁹)

| Comp'd | R⁸ | R⁹ | CAR 5 mg/kg (Escape Loss) IP Administration | Salt Form | M.p. (°C.) | Receptor Binding ($K_I$ nM) $D_2$ |
|---|---|---|---|---|---|---|
| 108 | 4-CO₂Et-cyclohexyl | | −69%(0) at 15 mg/kg | 1.8 HCl (0.7 hdrate) | 178–182 | 10.4 |
| 109 | 1-methyl-1-cyclohexyl (Me, Me) | | −67%(17%) | 2 HCl (hydrate) | 214–227 | 7.0 |
| 110 | 4-oxo-cyclohexyl (O) | | −31%(0) | 2 HCl (0.3 hydrate) | 218–220 | 32 |
| 111 | −(CH₂)₅− | | −95%(0) | 2 HCl | 192.5–196 | 37 |

TABLE 5-continued

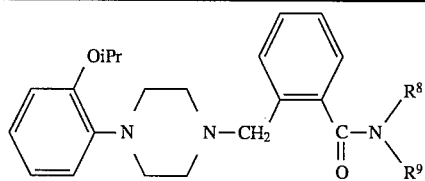

| Comp'd | R[8] | R[9] | CAR 5 mg/kg (Escape Loss) IP Administration | Salt Form | M.p. (°C.) | Receptor Binding ($K_I$ nM) $D_2$ |
|---|---|---|---|---|---|---|
| 112 | Me | $cC_5H_9$ | −98%(33%) | 2 HCl | 196–199 | 16 |
| 113 | −(CH$_2$)$_6$− | | −72%(12%) | 2 HCl (0.35 hydrate) | 208.5–210.5 | 11 |

TABLE 6

| CP # | Dose (mg/kg)[1] | Pre-Reaction Time (min) | Catalepsy (%) |
|---|---|---|---|
| 39 | 50 | 60 | 17.3 |
| 53 | 50 | 60 | 32.4 |
| 53 | 50 | 240 | 47.9 |
| 80 | 50 | 60 | 84.8 |
| 80 | 50 | 240 | 62.0 |
| 84 | 50 | 60 | 18.8 |
| 84 | 50 | 240 | 33.9 |
| 93 | 50 | 60 | 20.0 |
| 93 | 50 | 240 | 1.9 |
| 111 | 50 | 60 | 52 |
| 111 | 50 | 240 | 50.7 |

Note
[1]: IP Administration

TABLE 7

| Compound | 1 h | 4 h | IV |
|---|---|---|---|
| #53 | 0.038 [0.006, 0.056] | 0.263 [0.094, 0.439] | 0.030 [0.008, 0.045] |
| #54 | 0.047 [0.29, 0.86] | 0.251 [0.116, 0.801] | 0.019[a] |
| Haloperidol | 0.088 | 0.028[b] | 0.023[a] |

The $ED_{50}$ (mg/kg) values and 95% confidence limits are shown for oral administration (1 h and 4 h pretreatment) and for intravenous (IV) administration. Notes: a. $ED_{50}$ estimated using linear regression, 95% confidence limits not determined. b. $ED_{50}$ computed with PROBIT, 95% confidence limits not determined.

TABLE 8

| comp'd# | Route of Administration | Dose (mg/kg) | Expiration Time (min) |
|---|---|---|---|
| 31 | IP | 1.0 | 18 |
| 32 | IP | 1.0 | 41 |
| 33 | IP | 1.0 | 10 |
| 34 | PO | 10.0 | 33 |
| 35 | PO | 10.0 | 19 |
| 36 | PO | 10.0 | 7.4 |
| 37 | PO | 10.0 | 25 |
| 48 | IP | 1.0 | 14 |
| 54 | IP | 1.0 | 16 |
| 55 | IP | 1.0 | 13 |
| 56 | IP | 1.0 | 15 |
| 57 | IP | 1.0 | 22 |
| 58 | IP | 1.0 | 29 |
| 59 | IP | 1.0 | 43 |
| 60 | IP | 1.0 | 18 |
| 62 | IP | 1.0 | 21 |
| 63 | IP | 1.0 | 41 |
| 65 | IP | 1.0 | 28 |
| 66 | IP | 1.0 | 18 |
| 70 | IP | 1.0 | 14 |
| 71 | IP | 1.0 | 23 |
| 72 | IP | 1.0 | 29 |
| 73 | PO | 40.0 | 25 |
| 77 | IP | 1.0 | 12 |
| 78 | IP | 1.0 | 28 |
| 79 | IP | 1.0 | 17 |
| 80 | IP | 1.0 | 14 |
| 81 | IP | 1.0 | 22 |
| 82 | IP | 1.0 | 16 |
| 83 | IP | 1.0 | 21 |
| 84 | IP | 1.0 | 42 |
| 86 | IP | 1.0 | 22 |
| 87 | IP | 1.0 | 28 |
| 88 | IP | 1.0 | 29 |
| 89 | IP | 1.0 | 16 |
| 90 | IP | 1.0 | 27 |
| 92 | IP | 1.0 | 17 |
| 93 | IP | 1.0 | 25 |
| 103 | IP | 1.0 | 43 |
| 104 | PO | 10.0 | 50 |
| 105 | PO | 10.0 | 10 |
| 111 | IP | 1.0 | 11 |
| 112 | IP | 1.0 | 11 |
| 113 | PO | 10.0 | 15 |

We claim:

1. A compound represented by the formula I:

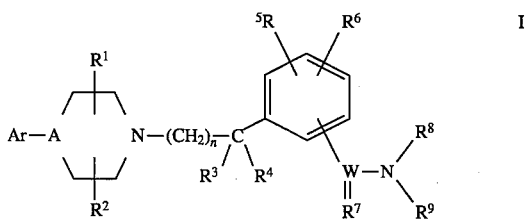

wherein

Ar is selected from either of phenyl or naphthyl either which can be optionally substituted with one or more of $C_1$–$C_8$ alkyl, cycloalkyl, $C_1$–$C_8$ alkoxy, aryloxy, hydroxyl, trifluoromethyl, trifluoromethoxy, cyano, $C_1$–$C_8$ alkylthio, halogen, nitro, $C_1$–$C_8$ haloalkyl, amino or mono- or dialkylamino wherein each alkyl is $C_1$–$C_8$, or heteroaryl selected from any of pyrimidinyl, pyridinyl, pyridazinyl, pyrazinyl, imidazyl, pyrrolyl, furanyl, thiophenyl, triazolyl and thiazolyl;

A is N;

W is C or SO;

$R^1$ and $R^2$ are H or $C_1$–$C_4$ alkyl;

n=0–4

$R^3$ and $R^4$ are either both H, or one of them is H and the other is $C_1$–$C_4$ alkyl or hydroxyl, or both are taken together as oxygen to constitute a carbonyl group, with the proviso that when n=0, $R^3$ and $R^4$ can not be taken together as oxygen;

$R^5$ and $R^6$ are independently selected from any one of H, $C_1$–$C_8$ alkyl, $C_1$–$C_8$ alkoxy, nitro, halogen, haloalkyl, $C_1$–$C_8$ alkylthio, amino, $C_1$–$C_8$ mono- or di-alkyl amino, or $C_1$–$C_8$ alkylamido;

$R^7$ is O or S where W is C; $R^7$ is O where W is SO;

$R^8$ and $R^9$ are independently selected from any one of H, $C_1$–$C_8$ alkyl, $C_1$–$C_8$ aminoalkyl, phenyl, phenyl substituted with one or more of $C_1$–$C_8$ alkyl, $C_1$–$C_8$ alkoxy, halogen, trifluoromethyl, $C_1$–$C_8$ alkylthio, dialkylamino (wherein each alkyl is $C_1$–$C_8$), $C_1$–$C_8$ alkylamino, nitro or mono- or dialkylamino sulfonyl (wherein each alkyl is $C_1$–$C_8$), aralkly wherein the alkyl portion is $C_1$–$C_8$, $C_1$–$C_8$ acyl, $C_3$ to $C_{10}$ cycloalkyl; provided that when $R^1$–$R^6$, $R^8$ and $R^9$ are hydrogen, W is SO, $R^7$ is O and A is nitrogen, Ar is not pyridyl; or —$NR^8R^9$ may be taken together to form a ring selected from any of pyrrolidine, piperidine, hexahydroazepine, octahydroazocine, oxazine or 2,6-dimethylpiperidine; provided that when Ar is unsubstituted Ph, $R^8R^9$ are not —$(CH^2)_5$—; when Ar is 2-pyrimidinyl, $R^8R^9$ are not

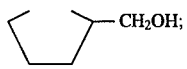

when Ar is 2(OiPr)Ph, $R^8R^9$ are not

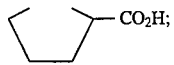

wherein Ar is 2,5(MeO)$_2$Ph, $R^8R^9$ are not —$(CH_2)_4$—; and when Ar is 2,6(MeO)$_2$Ph, $R^8R^9$ are not —$(CH_2)_5$; or optionally —$NR^8R^9$ may be taken together to form a fused bicyclic ring selected from either of formulas III or IV;

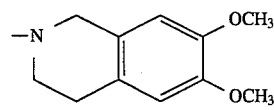

or

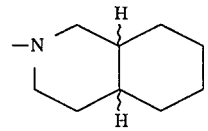

or optionally $NR^8R^9$ may be a spirocycle ring system of the formula V;

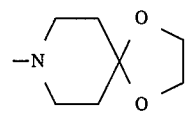

when —$NR^8R^9$ are taken together to form the 4–8 membered ring, the fused ring system or the spirocycle ring system, the rings may be optionally substituted with one or more of $C_1$–$C_8$ alkyl, $C_1$–$C_8$ alkoxy, phenyl, phenyl substituted with one or more of $C_1$–$C_8$ alkyl, $C_1$–$C_8$ alkoxy, halogen, trifluoromethyl, $C_1$–$C_8$ alkylthio, dialkylamino (wherein each alkyl is $C_1$–$C_8$), $C_1$–$C_8$ alkylamino, nitro, or mono- or di-alkylamino sulfonyl (wherein each alkyl is $C_1$–$C_8$), hydroxy, aralkyl wherein the alkyl portion is $C_1$–$C_8$; oxo or thioxo, or the pharamaceutically acceptable acid addition salt thereof.

2. The compound of claim 1 wherein Ar is a substituted or unsubstituted fused ring system selected from benzofuranyl, naphthyl, benzodioxanyl,

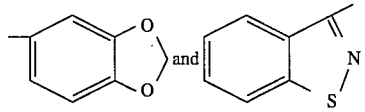

wherein the substituent is selected from any one of $C_1$–$C_5$ alkyl, $C_3$–$C_7$ cycloalkyl, phenyl, phenyl substituted with one or more $C_1$–$C_8$ alkyl, $C_1$–$C_8$ alkoxy, halogen, trifluoromethyl, $C_1$–$C_8$ alkylthio, di-alkylamino (wherein each alkyl is $C_1$–$C_8$), $C_1$–$C_8$ alkylamino, nitro or mono or di-alkylamino sulfonyl (wherein each alkyl is $C_1$–$C_8$), $C_1$–$C_5$ hydroxyalkyl, $C_1$–$C_5$ alkoxy, $C_1$–$C_5$ alkyl, $C_1$–$C_5$ alkoxy, aryloxy, $C_1$–$C_5$ alkylthio, arylthio, mono- or diarylamino, hydroxyl, amino, $C_1$–$C_5$ alkyl-, $C_1$–$C_5$ alkoxy-, amino-, mono- or di-alkylamino-carbonyl, wherein each alkyl is $C_1$–$C_5$, nitro, cyano, halogen, trifluoromethyl, trifluoromethoxy, amino-or mono- or di-alkylamino-sulphonyl wherein each alkyl is $C_1$–$C_5$.

3. The compound of claim 1 wherein Ar is a fused ring system selected from naphthyl, benzofuranyl, benzodioxanyl,

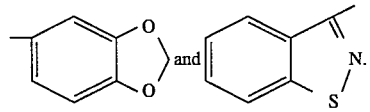

4. The compound of claim 1, wherein B forms together with the two carbon atoms of the phenyl group an entirely or partly unsaturated ring consisting of 5 ring atoms, at least one of which is an oxygen atom;

wherein $R^{10}$ and $R^{11}$ are independently selected from any one of alkyl, alkoxy, hydroxyl, nitro, cyano, halogen, trifluoromethyl, with the proviso that $R_6$ is the meta or ortho position in relation to the piperizine ring; wherein each of m and p has the value of 0–2.

5. The compound of claim 4, wherein m and p each equal 0.

6. The compound of claim 1, wherein Ar is phenyl substituted with an alkoxy group; n=0; and $R^1$, $R^2$, $R^3$, and $R^4$ are each H.

7. The compound of claim 6, wherein the alkoxy group is i-propoxy.

8. The compound of claim 1, wherein the 4–8 membered ring is unsubstituted.

9. The compound of claim 1, wherein the 4–8 membered ring is substituted with one or more of $C_1$–$C_8$ alkyl, $C_1$–$C_8$ alkoxy, phenyl, substituted phenyl, hydroxy, aralkyl, oxo or thio, wherein phenyl may be substituted with one or more of $C_1$–$C_8$ alkyl, $C_1$–$C_8$ alkyloxy, halogen, trifluoromethyl, $C_1$–$C_8$ alkythio, di-alkylamino wherein each alkyl $C_1$–$C_8$, $C_1$–$C_8$ alkylamino, nitro or mono- or di-alkylamino sulfonyl wherein each alkyl is $C_1$–$C_8$.

10. The compound of claim 6, wherein W is C, wherein $R^7$ is O and wherein each of $R^8$ and $R^9$ are H.

11. The compound of claim 6, wherein W is SO, wherein $R^7$ is O and wherein each of $R^8$ and $R^9$ are H.

12. The compound of claim 6, wherein W is C, wherein $R^7$ is S and wherein each of $R^8$ and $R^9$ is H.

13. The compound of claim 1, wherein Ar is substituted phenyl, and it is substituted with one or more of $C_1$–$C_8$ alkyl, $C_1$–$C_8$ alkoxy, cyano, $C_1$–$C_8$ alkylthio, halogen, haloaklyl, trifluoromethyl, amino, or mono- or di-alkylamino.

14. The compound of claim 1, wherein Ar is substituted with one or more of $C_1$–$C_8$ alkyl, $C_1$–$C_8$ alkoxy, halogen or $C_1$–$C_8$ haloalkyl and wherein —$NR^8R^9$ are taken together to form a saturated ring having 4–8 carbon ring atoms with the N being the only hetero atom in the ring.

15. A compound of the formula I(a):

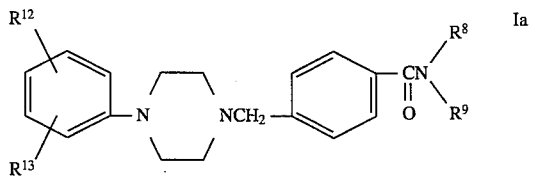

wherein $R^8$ and $R^9$ are each selected from any one of H, $C_1$–$C_8$ alkyl, phenyl, phenyl substituted with one or more of $C_1$–$C_8$ alkyl, $C_1$–$C_8$ alkoxy, halogen, trifluoromethyl, $C_1$–$C_8$ alkylthio, di-alkylamino (wherein each alkyl is $C_1$–$C_8$), $C_1$–$C_8$ alkylamino, nitro or mono- or di-alkylamino sulfonyl (wherein each alkyl is $C_1$–$C_8$), $C_6$–$C_{15}$ aralkyl, $C_1$–$C_8$ acyl, $C_4$–$C_{10}$ cycloalkyl; or —$NR^8R^9$ may be taken together to form a ring selected from any of pyrrolidine, piperidine, hexahydroazepine, octahydroazocine, oxazine or 2,6-dimethylpiperidine; or optionally —$NR^8R^9$ may be combined together to form a fused bicyclic ring selected from either of formulas III or IV;

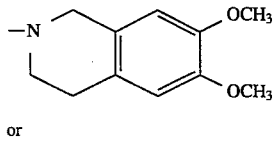

or

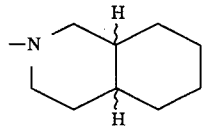

or optionally —$NR^8R^9$ may be taken together to form a spiro ring system of the formula V;

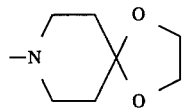

when —$NR^8R^9$ are taken together for form a 4–8 membered ring, a fused ring system or a spirocycle ring system, the rings may be substituted with one or more of $C_1$–$C_8$ alkyl, $C_1$–$C_8$ alkoxy, phenyl, phenyl substituted with one or more of $C_1$–$C_8$ alkyl, $C_1$–$C_8$ alkoxy, halogen, trifluoromethyl, $C_1$–$C_8$ alkylthio, di-alkylamino (wherein each alkyl is $C_1$–$C_8$), $C_1$–$C_8$ alkylamino, nitro or mono- or di-alkylamino sulfonyl (wherein each alkyl is $C_1$–$C_8$), hydroxy, aralkyl wherein the alkyl portion is $C_1$–$C_8$, oxo or thioxo; or wherein $R^{12}$ and $R^{13}$ are each selected from any one of H, $C_1$–$C_8$ alkyl, $C_1$–$C_8$ alkoxy, cyano, $C_1$–$C_8$ alkylthio, halogen, $C_1$–$C_8$ haloalkyl, amino, or $C_1$–$C_8$ mono- or di-alkylamino; or the pharmaceutically acceptable acid addition salts thereof.

16. The compound of claim 15 wherein $R^{12}$ is $C_1$–$C_8$ alkoxy.

17. The compound of claim 15 represented by the formula 1-[3-[[4-[2-(1-methylethoxy)phenyl]-1-piperazinyl]methyl]benzoyl]piperidine succinate.

18. The compound of claim 15 represented by the formula hexahydro-1-[3-[[4-[2-(1-methylethoxy)-phenyl]-1-piperazinyl]methyl]benzoyl]-1H-azepine monohydrochloride.

19. The compound of claim 15 represented by the formula 1[-3[[4-(1,4-benzodioxan-5yl)-1-piperazinyl]methyl]bnenzoyl]piperidine perchlorate (5:7).

20. The compound of claim 1 represented by the formula 1-[2-[[4-[2-(1-methylethoxy)phenyl]-1-piperazinyl]methyl]benzoyl]piperidine dihydrochloride.

21. The compound of claim 15 represented by the formula 1-[3-[[4-[2-(1-methylethyoxy)phenyl]-1-piperazinyl]methyl]benzoyl]-2,6-dimethylpiperidine [Hydrochloride]hydrochloride.

22. A pharmaceutical composition comprising the compound of claim 1, and a pharmaceutically acceptable carrier, said compound being present in a therapeutically effective amount for treating schizophrenia.

23. A method for treating schizophrenia in animals comprising adminstering to an animal in need of such treatment the compound of claim 1 in an amount sufficient to treat such condition.

24. The method claim 23, wherein Ar is phenyl substituted with $C_1$–$C_8$ alkoxy.

25. The method of claim 24, wherein the —$NR^8R^9$ ring has 4–8 carbon atoms.

26. The method of claim 23, represented by the formula 1-[3-[[4-[2-(1-methylethoxy)phenyl]-1-piperazinyl]methyl]benzoyl]piperidine succinate.

27. The method of claim 23, represented by the formula hexahydro-1-[3-[[4-[2-(1-methylethoxy)phenyl]-1-piperazinyl]methyl]benzoyl]-1H-azepine monohydrochloride.

28. The method of claim 23, represented by the formula 1-[3[[4-(1,4-benzodioxin-5-yl)-1-piperazinyl]methyl]benzoyl]piperidine perchlorate (5:7).

29. The method of claim 23, represented by the formula 1-[2-[[4-[2-(1-methoxyethoxy)phenyl]-1-piperazinyl]methyl]benzoyl]piperidine dihydrochloride.

30. The method of claim 23, represented by the formula 1-[3-[[4-[2-(1-methylethoxy)phenyl]-1-piperazinyl]methyl]benzoyl]-2,6-dimethylpiperidine hydrochloride.

* * * * *